United States Patent
Jo et al.

(10) Patent No.: US 9,251,964 B2
(45) Date of Patent: Feb. 2, 2016

(54) PORPHYRIN-BASED COMPOUND, DYE AND DYE-SENSITIZED SOLAR CELL COMPRISING THE SAME

(71) Applicant: DAEGU GYEONGBUK INSTITUTE OF SCIENCE AND TECHNOLOGY, Daegu (KR)

(72) Inventors: Hyojeong Jo, Daegu (KR); Jungeun Nam, Daegu (KR); Daehwan Kim, Daegu (KR); Jinkyu Kang, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 30 days.

(21) Appl. No.: 14/229,807

(22) Filed: Mar. 28, 2014

(65) Prior Publication Data

US 2015/0096618 A1    Apr. 9, 2015

(30) Foreign Application Priority Data

Oct. 7, 2013 (KR) .......................... 10-2013-0118953

(51) Int. Cl.
| | |
|---|---|
| *H01G 9/20* | (2006.01) |
| *C09B 47/00* | (2006.01) |
| *H01L 51/00* | (2006.01) |
| *C07D 487/22* | (2006.01) |

(52) U.S. Cl.
CPC ............ *H01G 9/2059* (2013.01); *C07D 487/22* (2013.01); *C09B 47/00* (2013.01); *H01L 51/0077* (2013.01); *H01G 9/2031* (2013.01); *H01L 51/0092* (2013.01)

(58) Field of Classification Search
CPC ....... C07D 487/22; C09B 47/00; C09B 47/45

USPC .......................................................... 13/253
See application file for complete search history.

(56) References Cited

FOREIGN PATENT DOCUMENTS

| CN | 100361994 C | 1/2008 |
|---|---|---|
| JP | 2002-063949 A | 2/2002 |
| KR | 10-0809496 B1 | 2/2008 |
| KR | 10-0890496 B1 | 3/2009 |
| KR | 10-2013-0066547 A | 6/2013 |

OTHER PUBLICATIONS

Kano et al, Regulation of alpha-chymotrypsin catalysis by ferric porphyrins and cyclodextrins, 2008, Chemistry—An Asian Journal, vol. 3, pp. 678-686.*
Korean Official Action, in Korean language, four pages, mailed Apr. 20, 2015.
Li et al., "Electrochemical-Coupling Layer-by-Layer (ECC-LbL) Assembly", J. Am. Chem. Soc., vol. 133, pp. 7348-7351, (2011).
Notice of Allowance for corresponding Korean Patent Application No. 10-2013-0118953, two pages, mailed Aug. 4, 2015.

* cited by examiner

*Primary Examiner* — Jonathan Johnson
*Assistant Examiner* — Bethany L Martin
(74) *Attorney, Agent, or Firm* — Vorys, Sater, Seymour and Pease LLP

(57) ABSTRACT

A porphyrin-based compound is represented by Chemical Formula 1 or 2. A dye for a dye-sensitized solar cell includes the porphyrin-based compound so that the dye has improved photoelectric conversion efficiency. A dye-sensitized solar cell includes a first electrode, a second electrode, and a dye layer formed between the first electrode and the second electrode, and the dye layer includes the porphyrin-based compound.

8 Claims, 2 Drawing Sheets

PORPHYRIN-BASED COMPOUND, DYE AND DYE-SENSITIZED SOLAR CELL COMPRISING THE SAME

CROSS REFERENCE TO RELATED APPLICATIONS AND CLAIM OF PRIORITY

This application claims priorities to and the benefit of Korean Patent Application No. 10-2013-0118953, filed on Oct. 7, 2013, the entire disclosure of which is incorporated herein by reference.

BACKGROUND

1. Field of the Invention

The present invention relates to a porphyrin-based compound, a dye including the same and a dye-sensitized solar cell, and more particularly, to a dye for a dye-sensitized solar cell, having improved photoelectric conversion efficiency, and to a dye-sensitized solar cell including the same.

2. Description of the Related Art

A solar cell for converting light energy into electric energy using a photovoltaic effect is an eco-friendly energy source using infinite resources, unlike the other energy sources. It is known to be a silicon solar cell, a dye-sensitized solar cell, etc.

A silicon solar cell is manufactured at very high cost and is thus difficult to actually use, and its efficiency is also difficult to improve. On the other hand, because a dye-sensitized solar cell is much lower in manufacturing cost than the conventional silicon solar cell, it has the potential to replace the conventional amorphous silicon solar cell. The dye-sensitized solar cell has a mechanism of absorbing visible light energy to thus produce electron-hole pairs, and is a photoelectrochemical solar cell composed mainly of a transition metal oxide for transferring produced electrons and a photosensitive dye molecule.

Currently useful as a dye for a dye-sensitized solar cell, a ruthenium complex exhibits an energy conversion efficiency of more than 10% and thereby has received academic attention, but has not yet been commercialized due to low stability which is a major problem concerning the complex-based dye.

To overcome such a problem, novel organic compounds are being studied as the dye. Especially, thorough research into using, as a dye, a porphyrin compound well-known to be a photosynthesis material, has been carried out, but its efficiency is about 1 to 3% which is not high. Hence, the Durrant research team of Imperial College in the UK reported that the reason why the efficiency of the porphyrin dye is lower than that of the ruthenium complex is that the porphyrin dye in an excited state is converted into a ground state by dipole-dipole attraction between adjacent porphyrin compounds.

Meanwhile, Japanese Patent Publication Application No. 2002-063949 (2002 Feb. 28) discloses a porphyrin derivative having photoelectric conversion properties, wherein phenyl groups are substituted at 5, 10, 15 and 20 positions of porphyrin, as represented below. However, such a porphyrin compound suffers from low energy conversion efficiency because of recombination of excited electrons between porphyrin dyes.

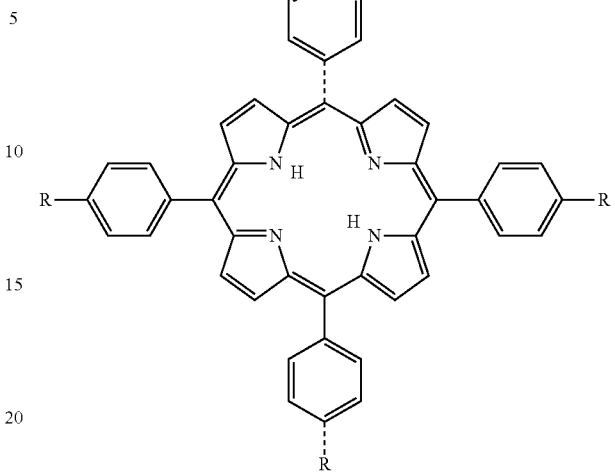

(wherein R is a hydrogen atom or an acidic substituent)

Also, Korean Patent No. 10-0809496 discloses a porphyrin derivative configured such that an amine group or an ether group is linked to phenyl groups substituted at 5, 10, 15 and 20 positions of porphyrin in order to extend conjugation, and Korean Patent Publication Application No. 10-2013-0066547 discloses a porphyrin derivative configured such that an amine group is substituted at 5 position of porphyrin and phenyl groups are substituted at 10, 15 and 20 positions of porphyrin.

Although the porphyrin compounds thus disclosed may prevent recombination between dyes compared to the porphyrin derivative of Japanese Patent Publication Application No. 2002-063949, only a single electron acceptor may be provided, making it difficult to increase adsorption of dye on the surface of $TiO_2$, consequently showing low energy conversion efficiency.

Therefore, there is a need to develop a porphyrin derivative for a dye-sensitized solar cell, having superior long-term stability compared to a ruthenium complex and superior photoelectric conversion efficiency compared to conventional porphyrin dyes.

SUMMARY

Accordingly, the present invention has been made keeping in mind the above problems encountered in the related art, and an object of the present invention is to provide a high-efficiency compound for a dye-sensitized solar cell and a dye-sensitized solar cell using the same, wherein such a compound may be easily synthesized and has high photoelectric conversion efficiency, and also a porphyrin derivative may be introduced with a variety of substituents, thereby solving difficulty in application to devices due to poor long-term stability which is the major problem of a conventional ruthenium dye, and overcoming low efficiency of a solar cell using a conventional porphyrin derivative.

In order to accomplish the above object, an aspect of the present invention provides a compound represented by Chemical Formula 1 and/or Chemical Formula 2 below.

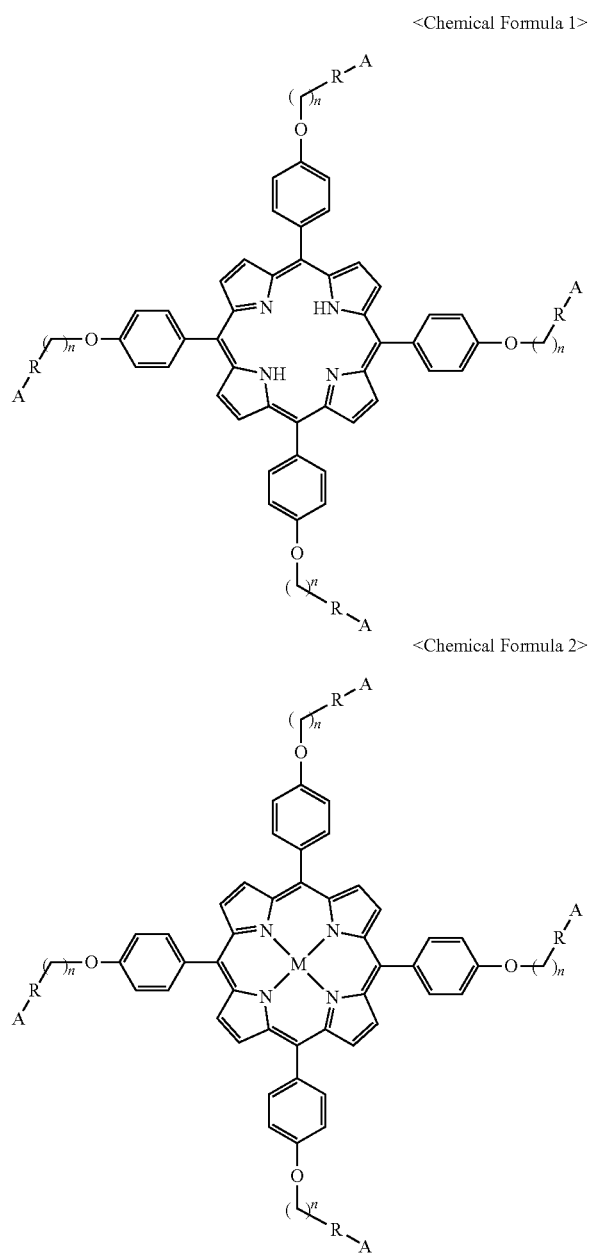

<Chemical Formula 1>

<Chemical Formula 2>

Another aspect of the present invention provides a dye including the compound represented by at least one of Chemical Formulas as above.

A further aspect of the present invention provides a dye-sensitized solar cell, comprising a first electrode; a second electrode; and a dye layer formed between the first electrode and the second electrode, wherein the dye layer includes at least one of organic dyes represented by Chemical Formula 1 or 2.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
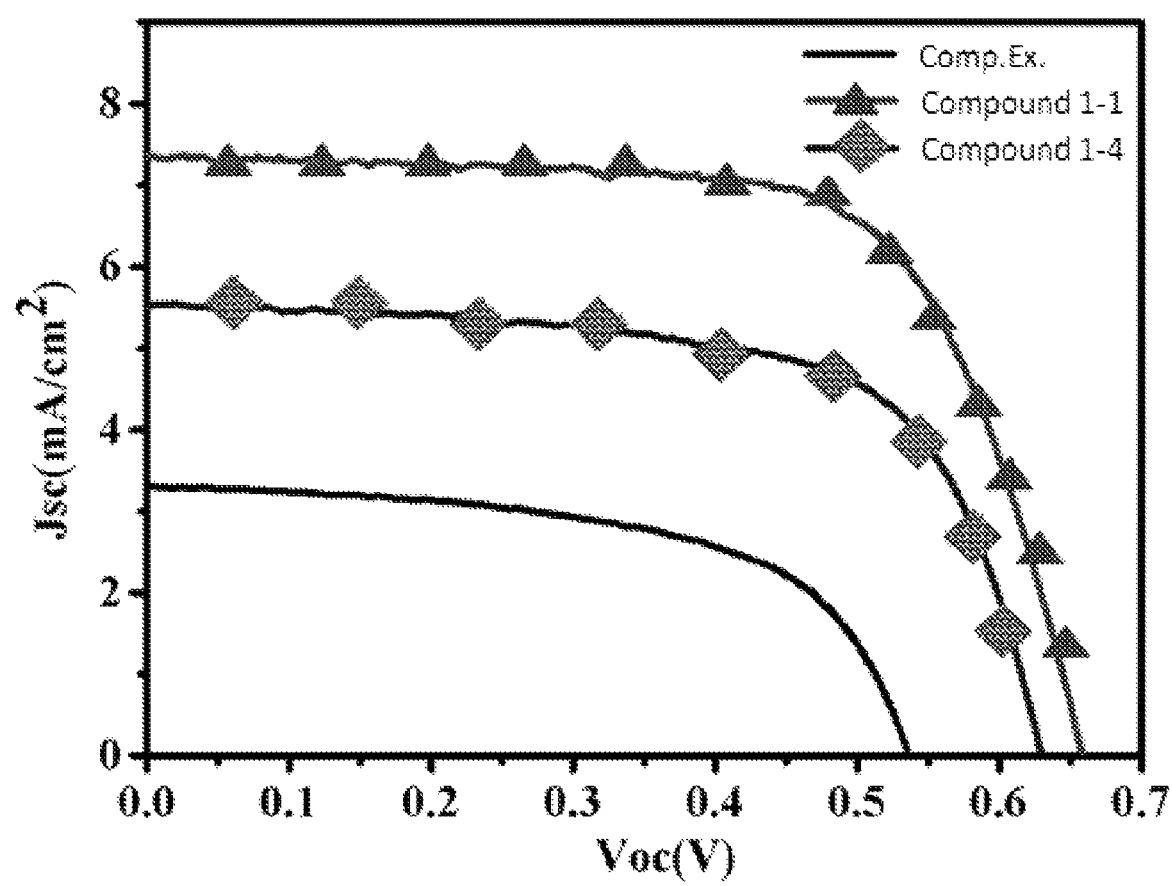
FIG. 1 is a graph illustrating current-voltage properties of a dye-sensitized solar cell including an organic dye according to an embodiment of the present invention.

Hereinafter, a detailed description will be given of embodiments of the present invention so that they may be easily performed by those skilled in the art with reference to the appended drawings. The present invention may be embodied in different forms and is not limited to the embodiments herein. In the following description, it is to be noted that, when a detailed description of known techniques related with the present invention may make the gist of the present invention unclear, it will be omitted.

As used herein, the term "halo" or "halogen" includes fluorine, chlorine, bromine and iodine unless otherwise mentioned, and the term "alkyl" or "alkyl group" includes a linear or branched chain unless otherwise mentioned.

As used herein, the term "alkenyl" or "alkynyl" includes a linear or branched chain having 2 to 60 carbon atoms with at least one double bond or triple bond, unless otherwise mentioned.

As used herein, the term "aryl group" or "arylene group" refers to a monocyclic or polycyclic aromatic group, and includes an aromatic ring formed by participation of the adjacent substituent in bonding or reaction. Examples of the aryl group may include a phenyl group, a biphenyl group, a fluorene group, a spirofluorene group, etc.

As used herein, the term "heterocyclic group" refers to a ring compound containing at least one heteroatom of N, O, S, P and Si with 2 to 60 carbon atoms, unless otherwise mentioned, and includes a monocyclic or polycyclic ring, and may also be formed by bonding of the adjacent group. Furthermore, the term "heterocyclic group" may indicate an alicyclic and/or aromatic group containing a heteroatom.

A dye-sensitized solar cell includes a first electrode formed on a first substrate, a second electrode formed on a second substrate and located to face the first electrode, an electrolyte solution charged between the first electrode and the second electrode, a nano oxide layer formed on the first electrode, a dye adsorbed onto the nano oxide layer, and a counter electrode located on the second electrode.

The surface of the nano oxide layer is adsorbed with the dye. The dye is a material which directly participates in production of photoelectrons, and it is favorable so long as absorption occurs over the entire visible light range and it has a higher light absorption coefficient.

Below is a detailed description of embodiments of the present invention, which are not construed as limiting the scope of the present invention.

According to an aspect of the present invention, an organic dye includes a compound represented by Chemical Formula 1 and/or Chemical Formula 2 below.

<Chemical Formula 1>

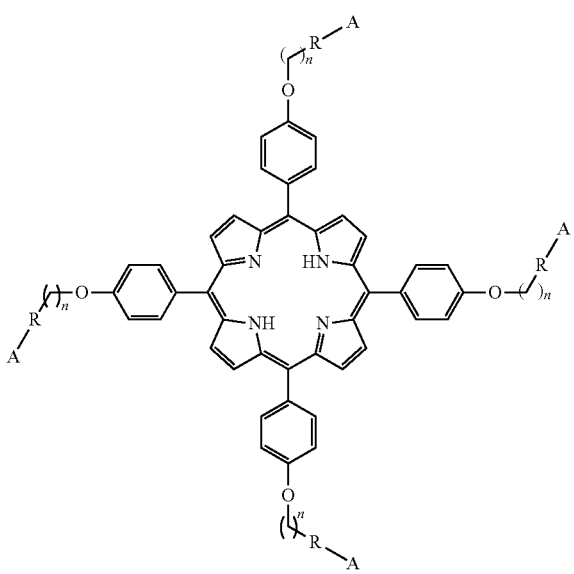

<Chemical Formula 2>

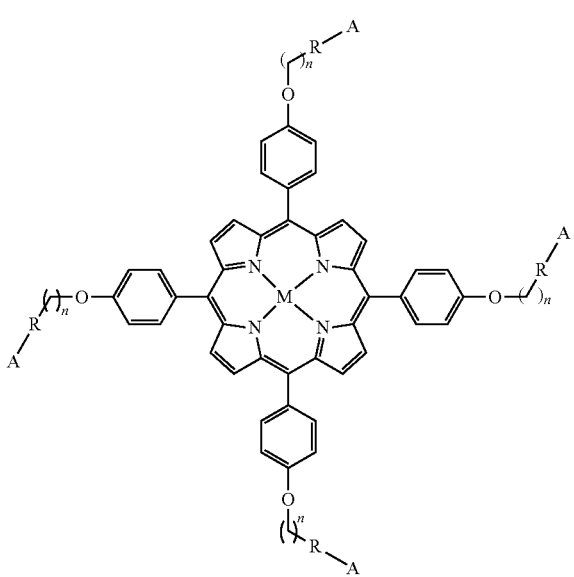

In Chemical Formulas 1 and 2, M is Zn or Pt, and n is independently an integer of 1 to 20.

Also, R is independently selected from the group consisting of a $C_6$-$C_{60}$ arylene group; a fluorenylene group; a $C_2$-$C_{60}$ heterocyclic group containing at least one heteroatom of O, N, S, Si and P; and

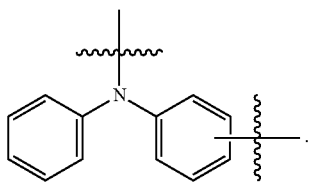

A is independently selected from the group consisting of a $C_1$-$C_{30}$ alkyl group; a $C_2$-$C_{30}$ alkenyl group; a $C_2$-$C_{30}$ alkynyl group; a $C_6$-$C_{60}$ aryl group; a $C_2$-$C_{60}$ heterocyclic ring containing at least one heteroatom of O, N, S, Si and P; and

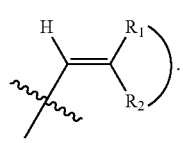

As such, $R_1$ and $R_2$ are able to form a $C_6$-$C_{60}$ aromatic ring or a heterocyclic ring containing at least one heteroatom of O, N, S, Si and P, together with carbon linked therewith, and —$CH_2$— of the aromatic ring or the heterocyclic ring may be replaced with —C=S or —C=O. Furthermore, A includes at least one carboxyl group. For example, in the case of an aryl group, any carbon for forming a ring may be substituted with at least one carboxyl group.

As such, a heterocyclic ring formed by linkage of $R_1$ and $R_2$ refers to a ring compound containing at least one heteroatom of O, N, S, Si and P. In this heterocyclic ring, $CH_2$ for forming a ring such as

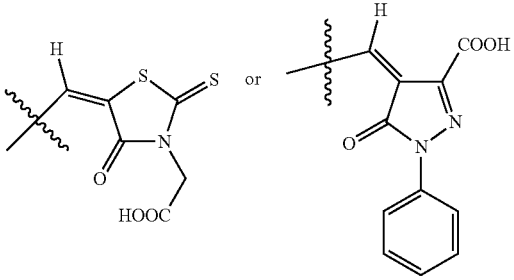 [SMILES: */C=C1/SC(=S)N(CC(=O)O)C1=O ; */C=C1\C(=O)N(c2ccccc2)N=C1C(=O)O]

may be replaced with C=S, C=O or the like, and as well, hydrogen linked to carbon for forming a ring or a heteroatom may be substituted with a carboxyl group.

Each of the aryl group, fluorenyl group, heterocyclic ring, alkyl group, alkenyl group, alkynyl group, arylene group, fluorenylene group and aromatic ring may be further substituted with one or more substituents selected from the group consisting of a carboxyl group, a hydroxyl group, halogen, a silane group, a boron group, a cyano group, a nitro group, an aryl group or a heterocyclic-substituted amine group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_6$-$C_{20}$ aryl group, a $C_2$-$C_{20}$ heterocyclic group, a $C_3$-$C_{20}$ cycloalkyl group, a $C_7$-$C_{20}$ arylalkyl group and a $C_8$-$C_{20}$ arylalkenyl group.

When A is an alkenyl group, at least one hydrogen of the alkenyl group may be substituted with a carboxyl group, and also with a cyano group, an aryl group, or a heterocyclic ring. For example, the case where A includes both a carboxyl group and a cyano group may result in

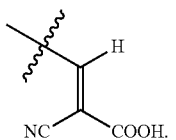 [SMILES: */C=C(\C#N)C(=O)O]

In another embodiment of the present invention, R may be represented by any one of the following compounds.

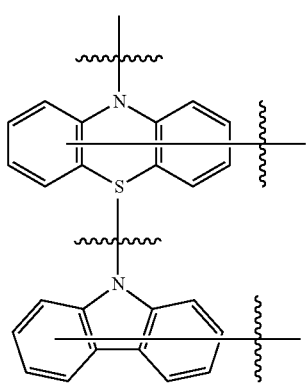
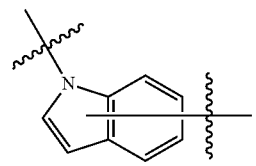
In another embodiment of the present invention, the compound represented by Chemical Formula 1 may be any one of the following compounds.
1-1
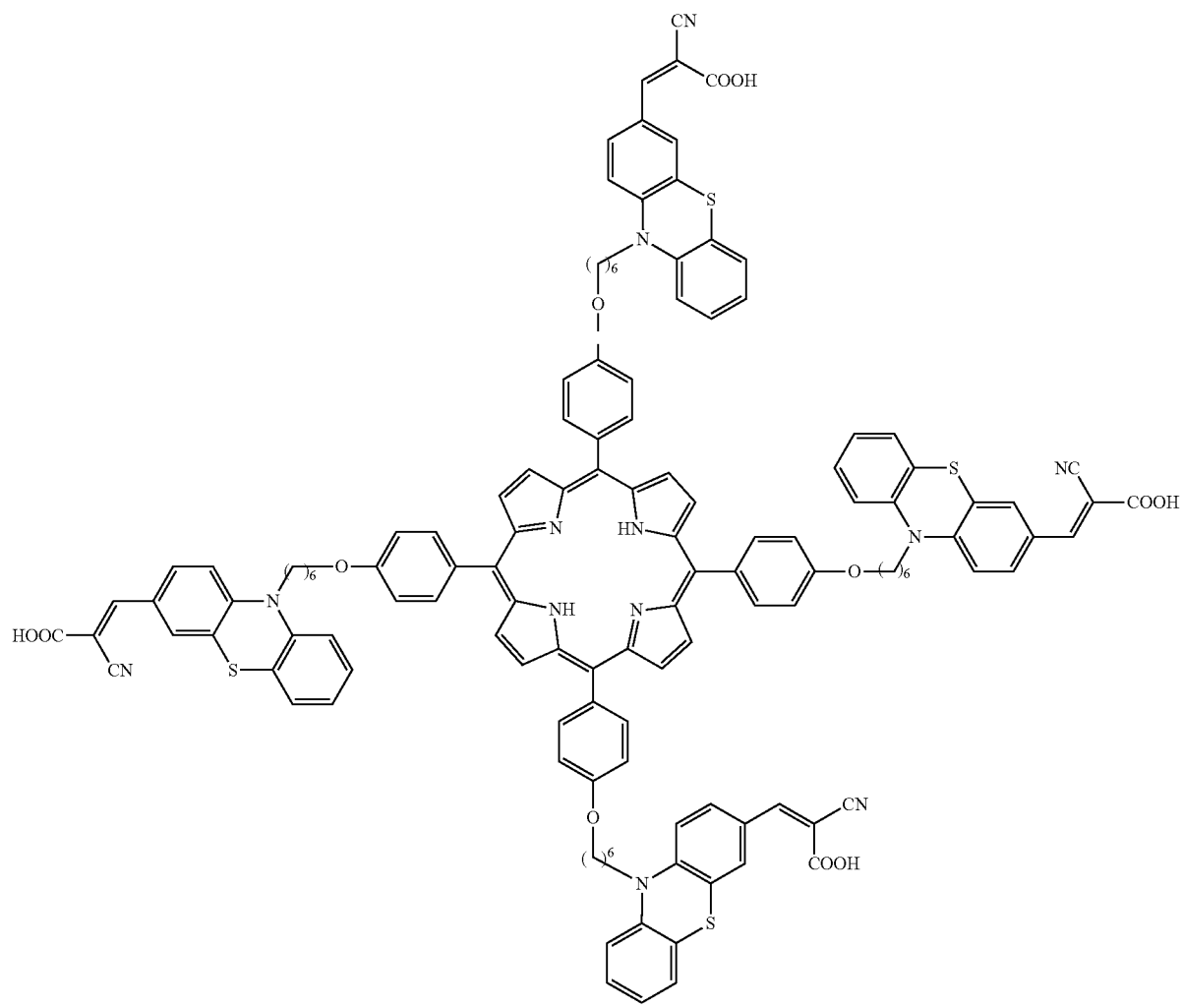

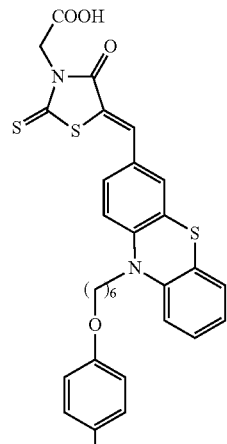
1-2
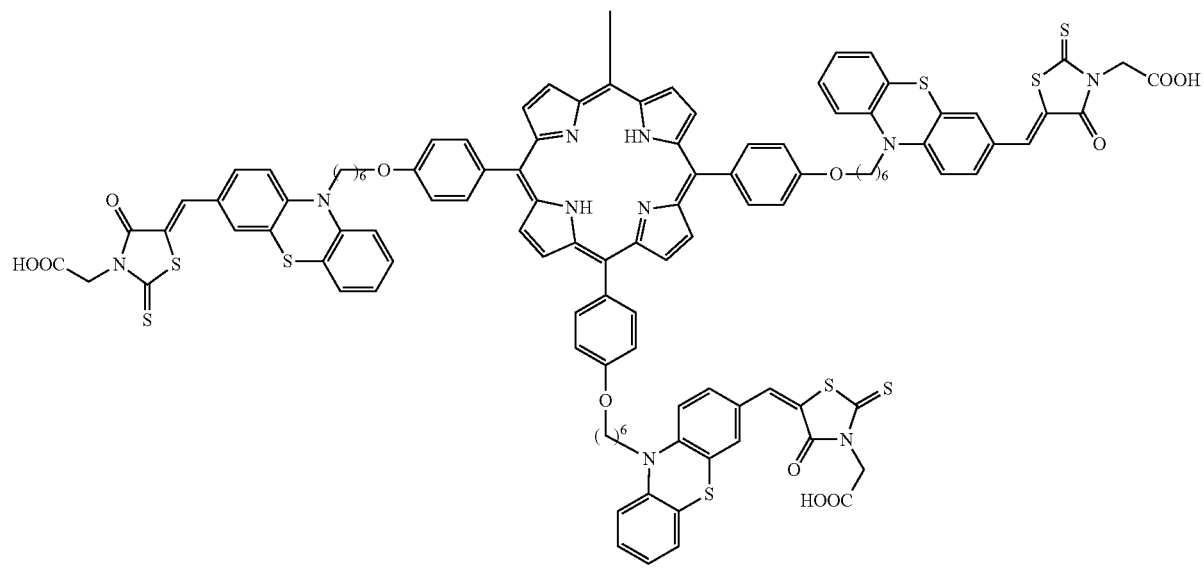
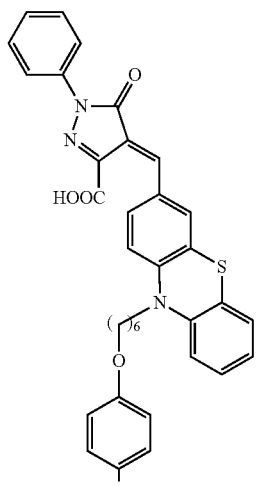
1-3

11 12
-continued
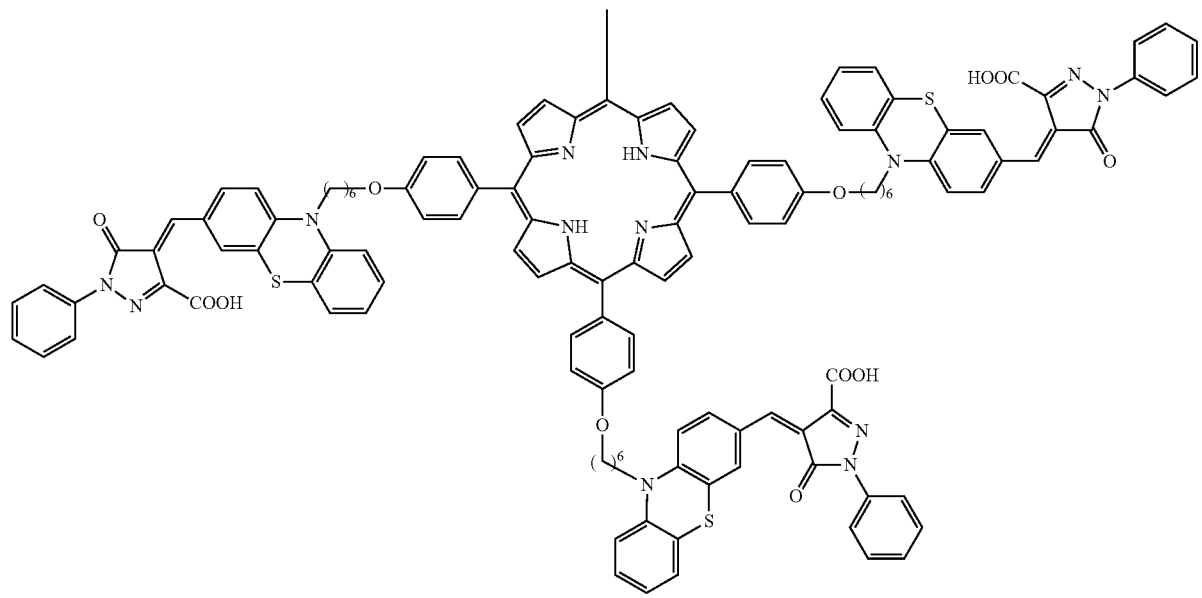
1-4
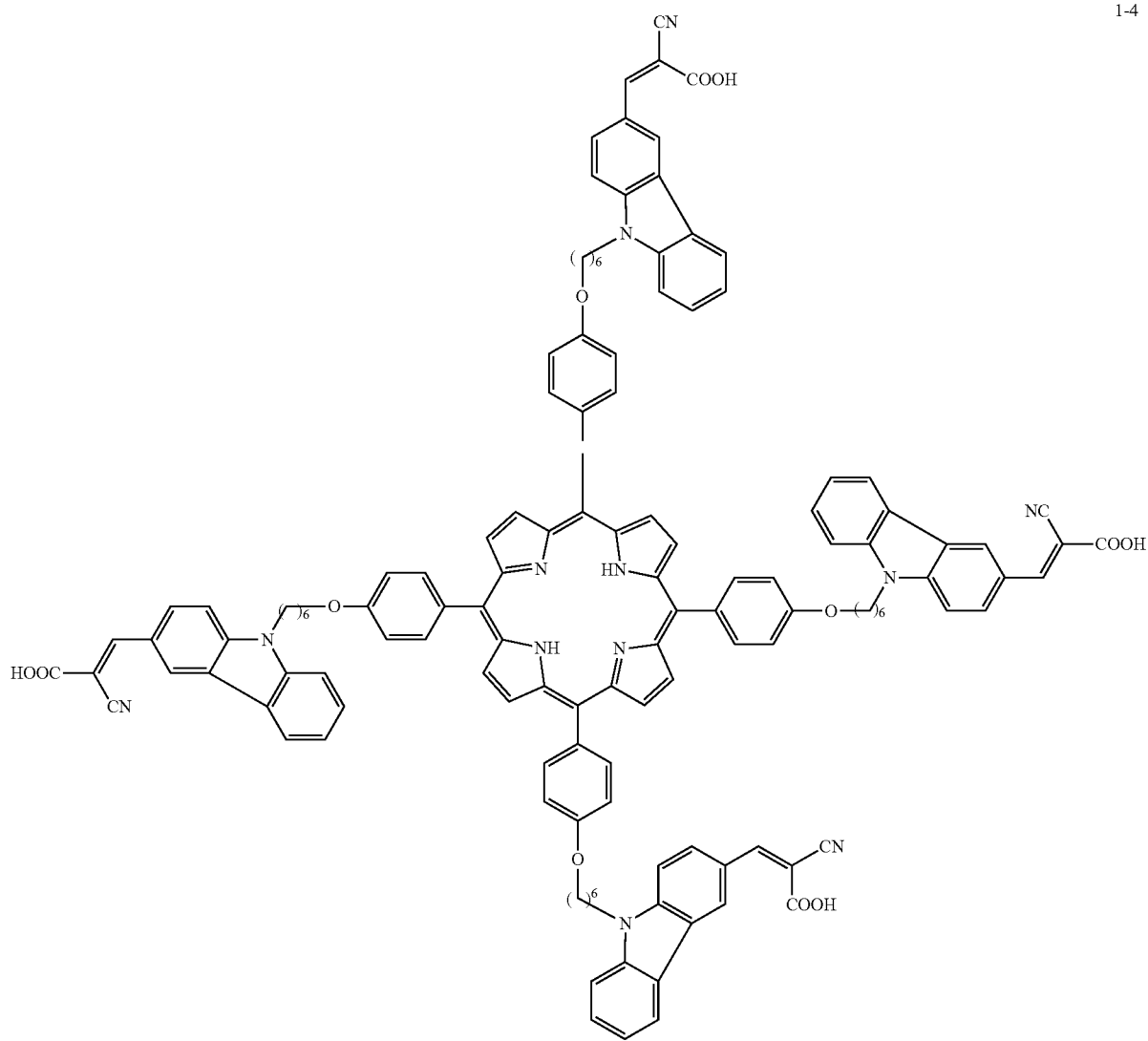

-continued
1-5
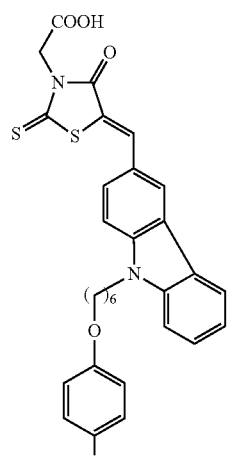
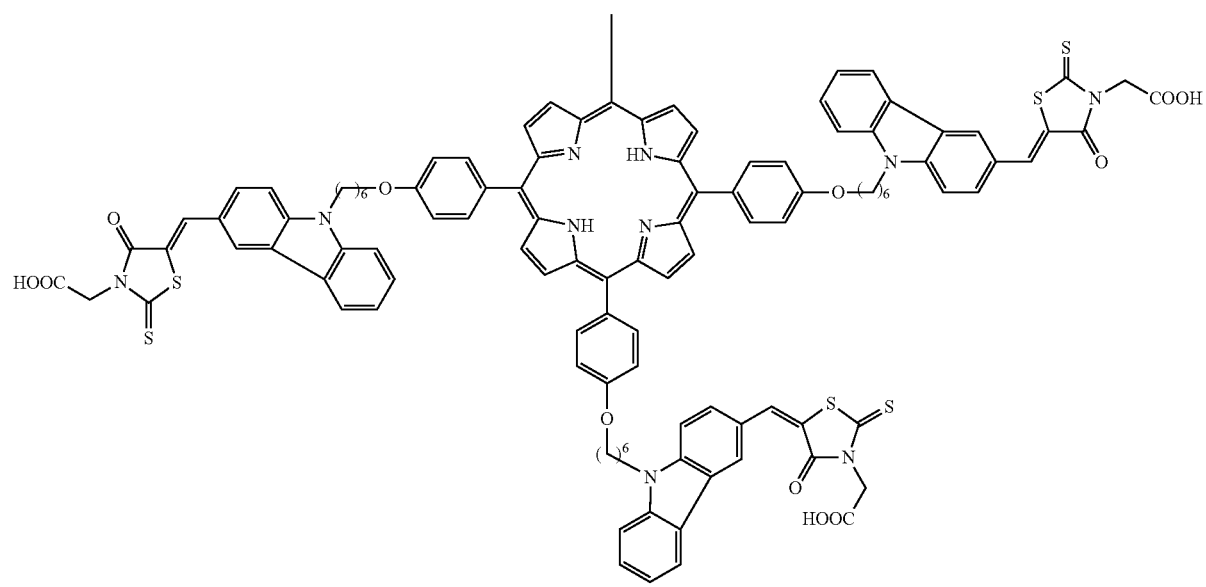
1-6
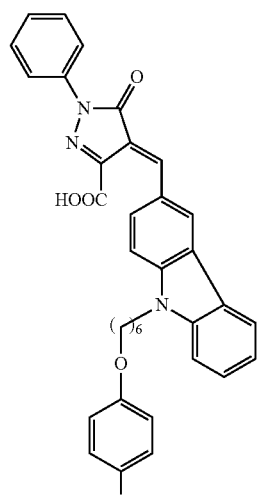

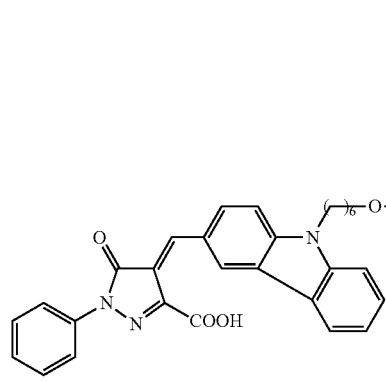
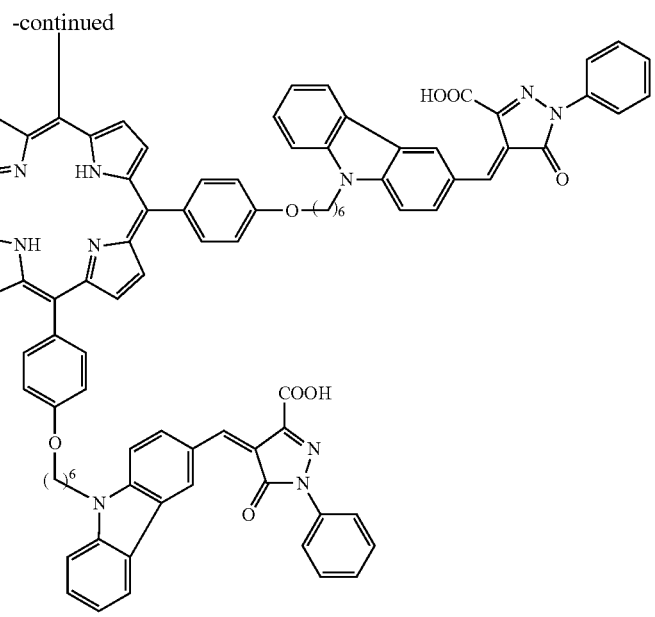
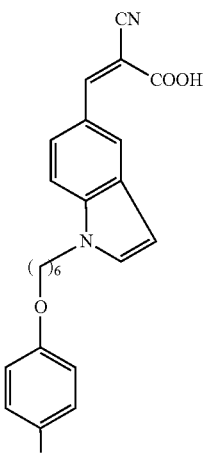
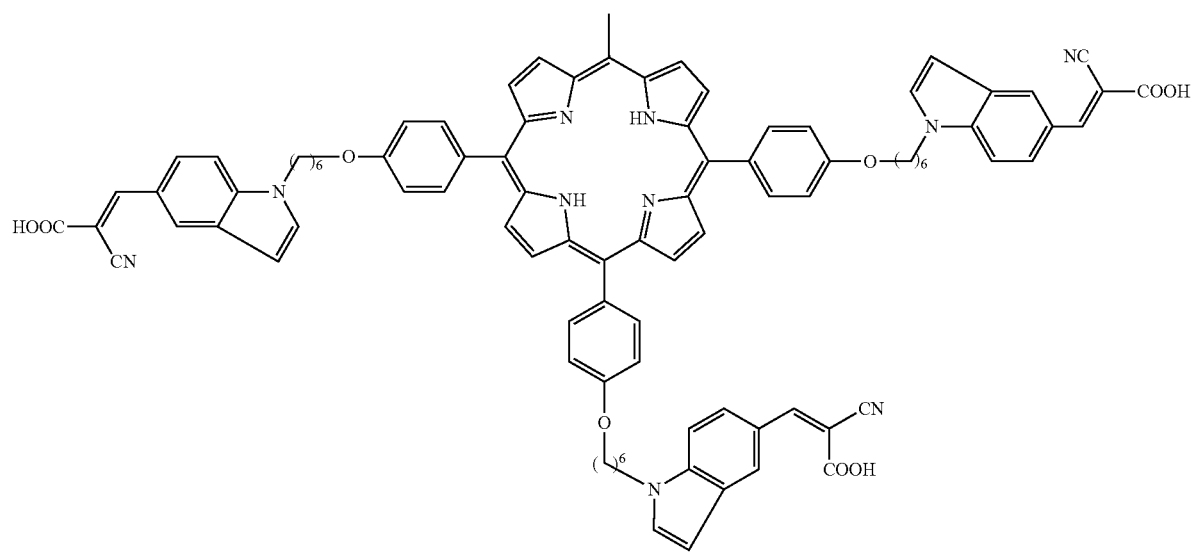

1-8
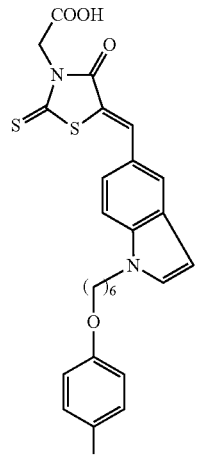
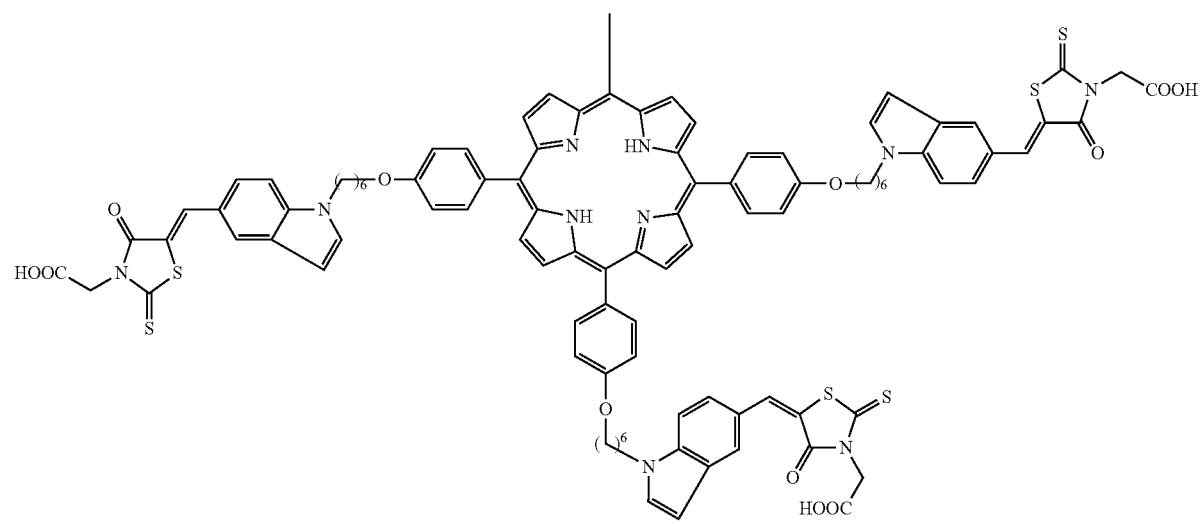
1-9
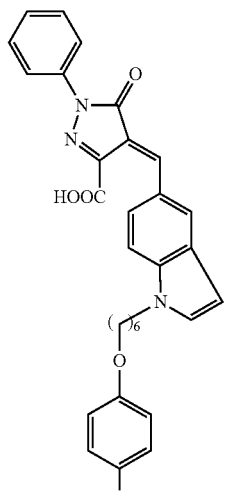

-continued
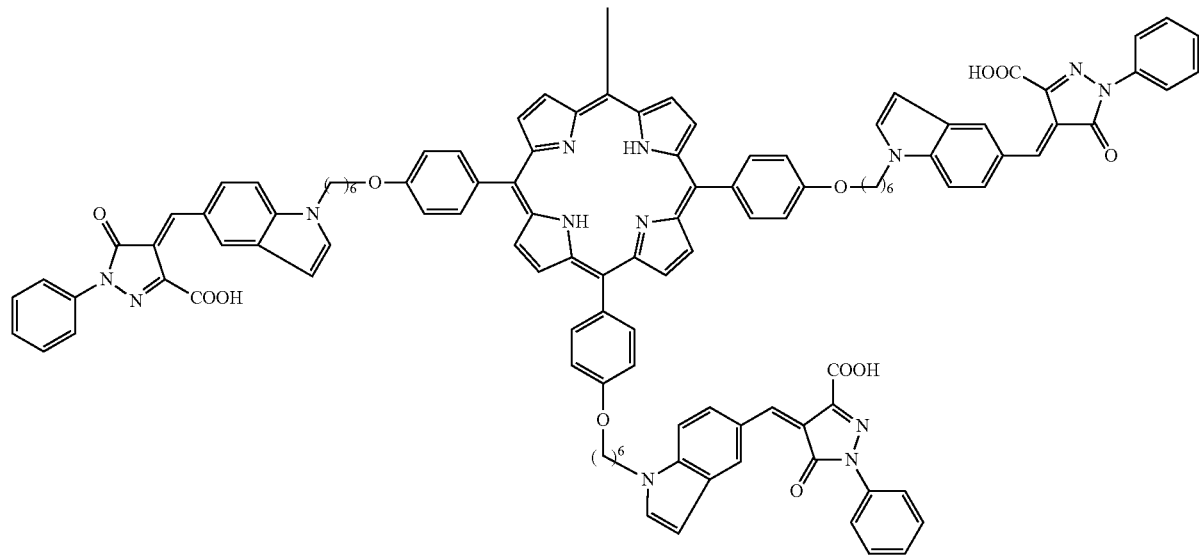
1-10
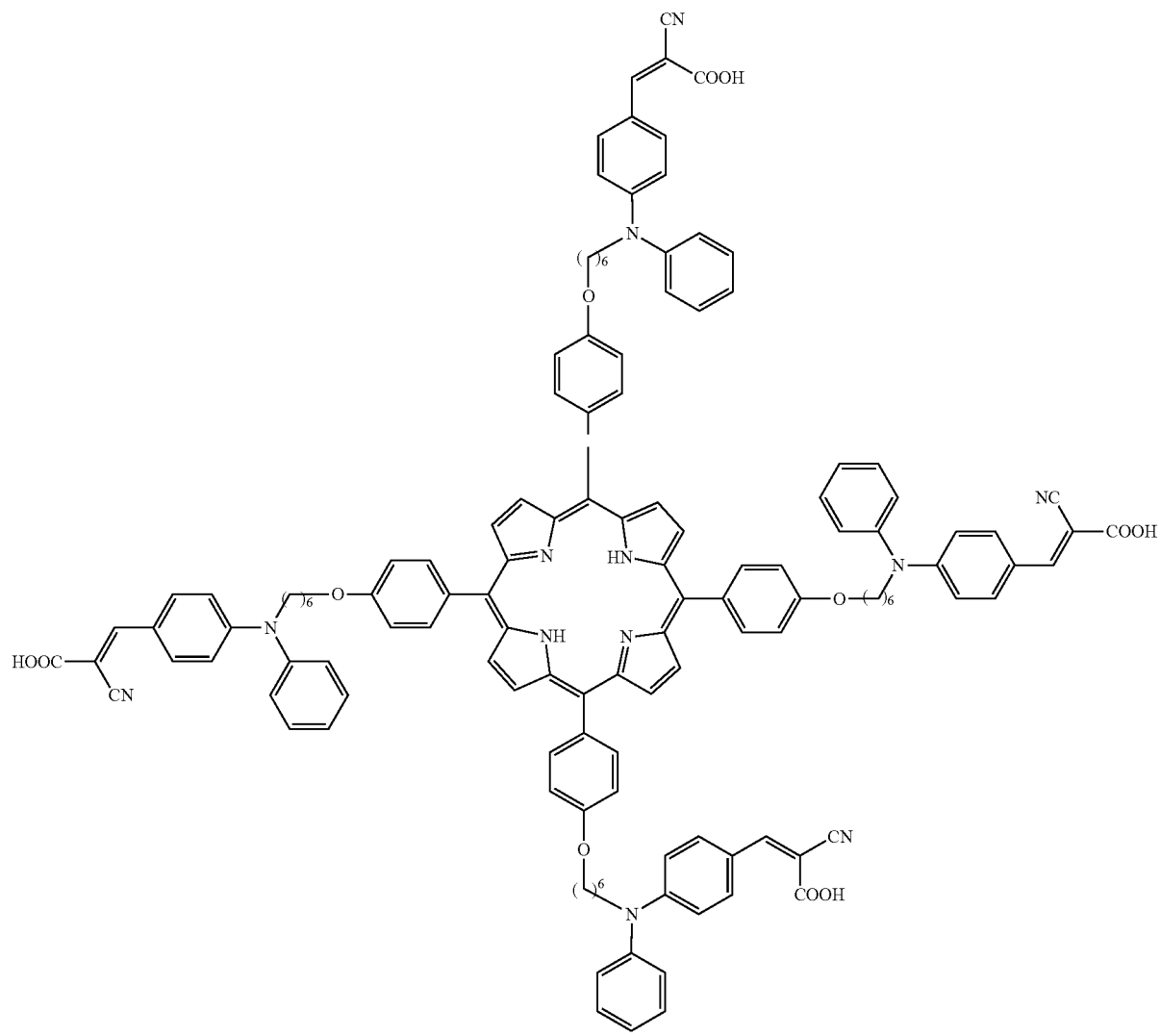

-continued
1-11
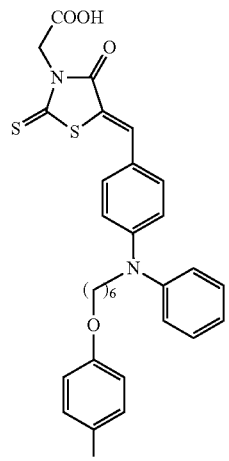
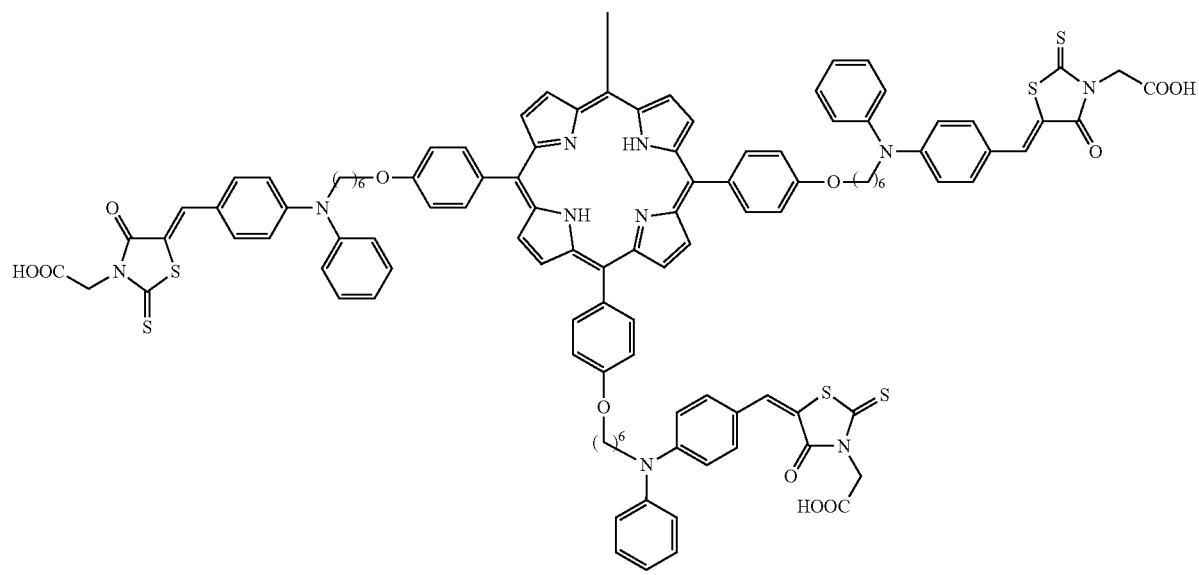
1-12
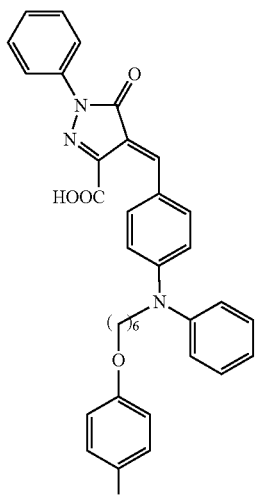

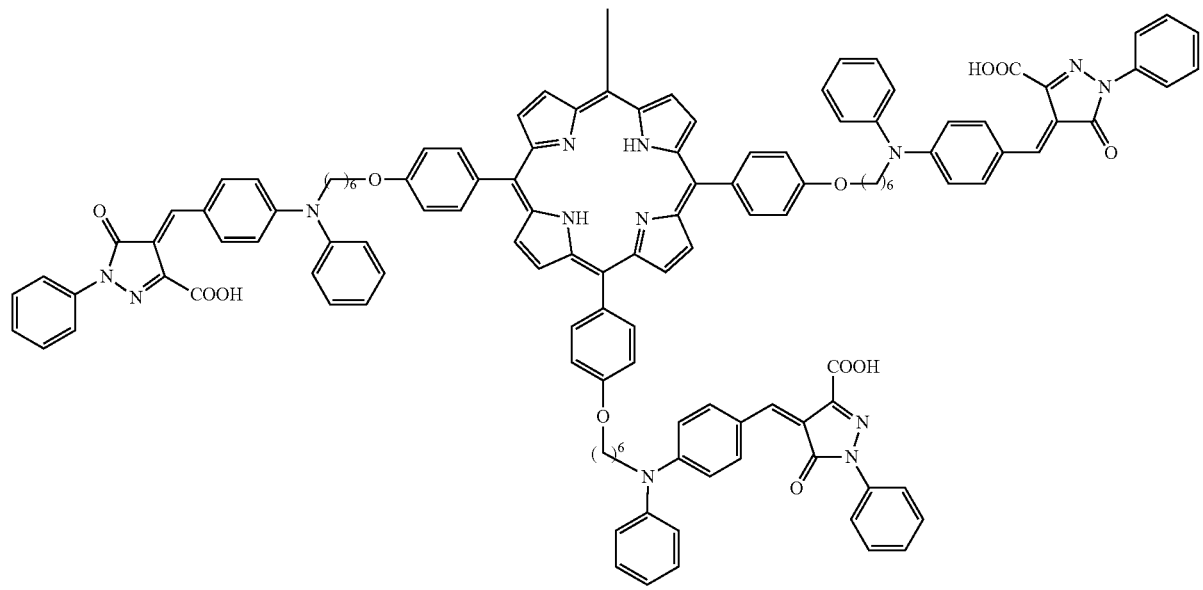
In another embodiment of the present invention, the compound represented by Chemical Formula 2 may be any one of the following compounds.
2-1
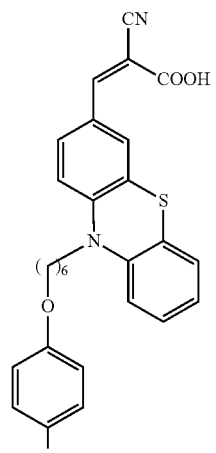

-continued
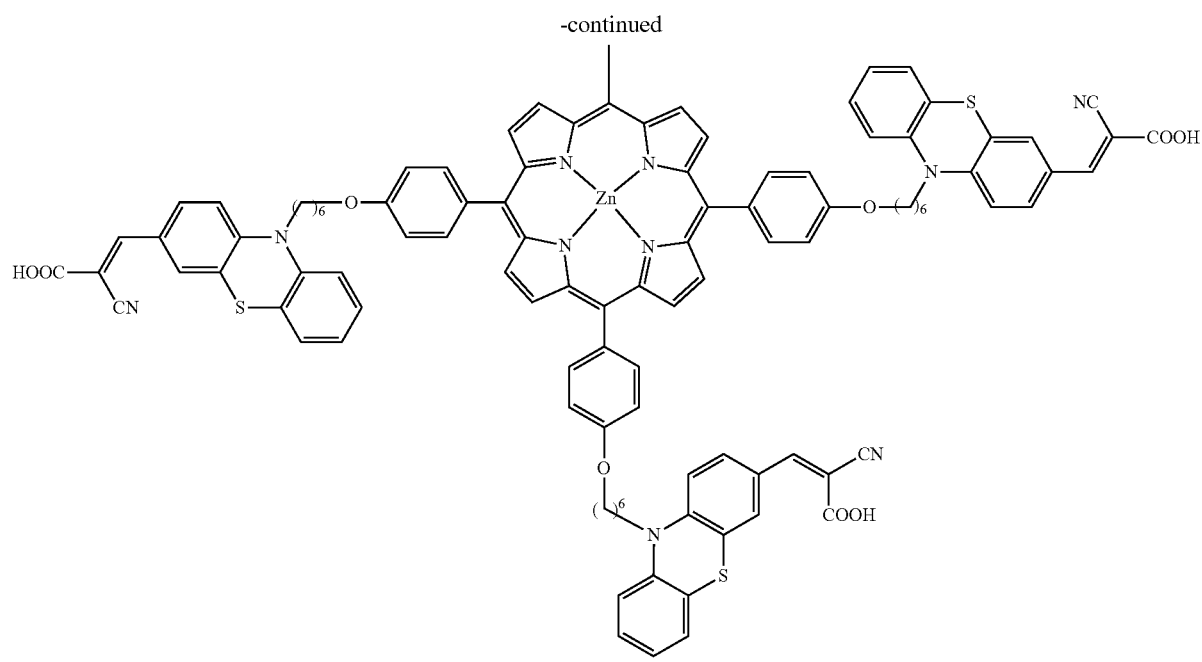
2-2
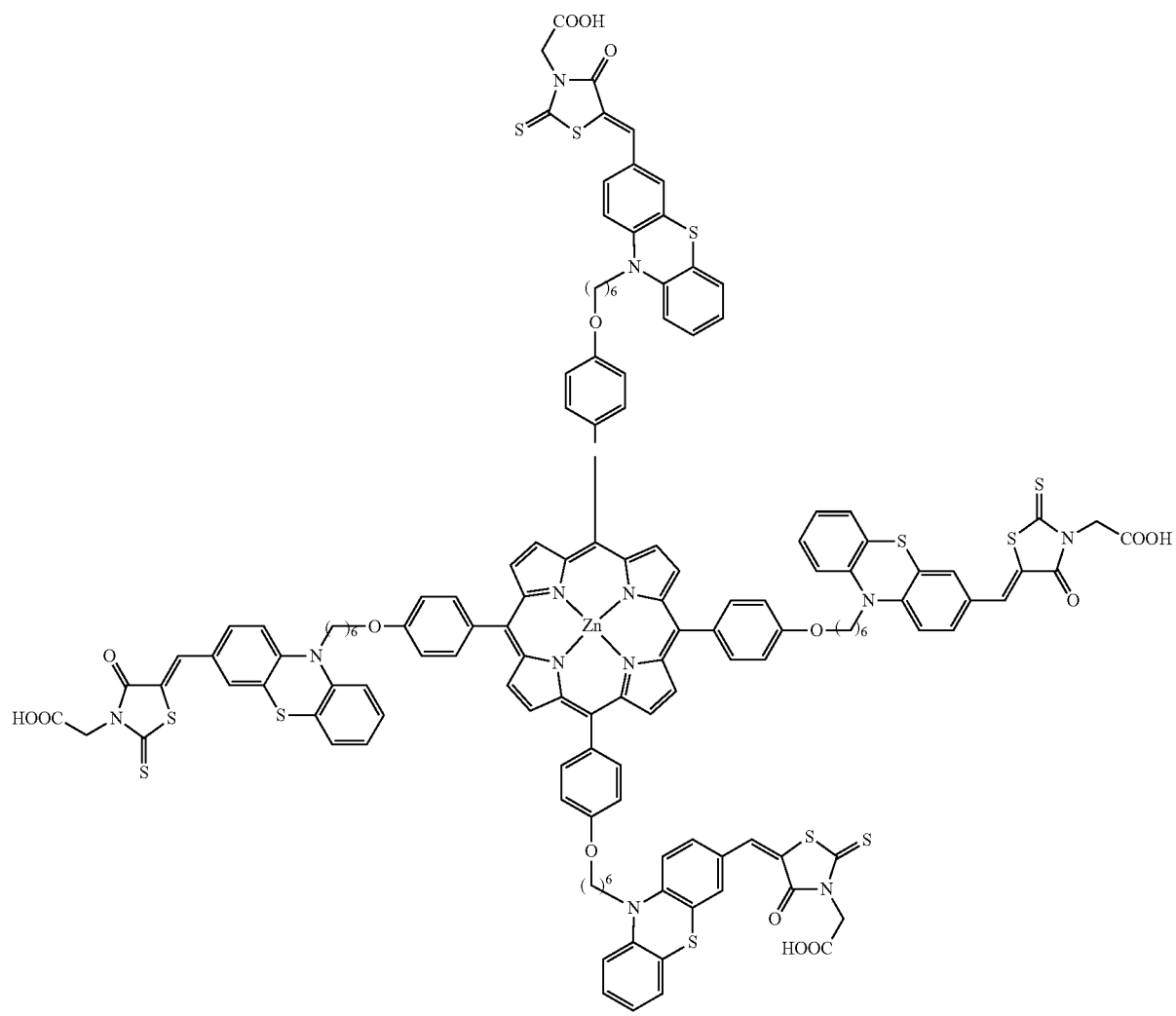

2-3
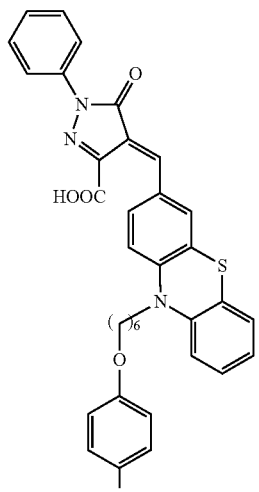
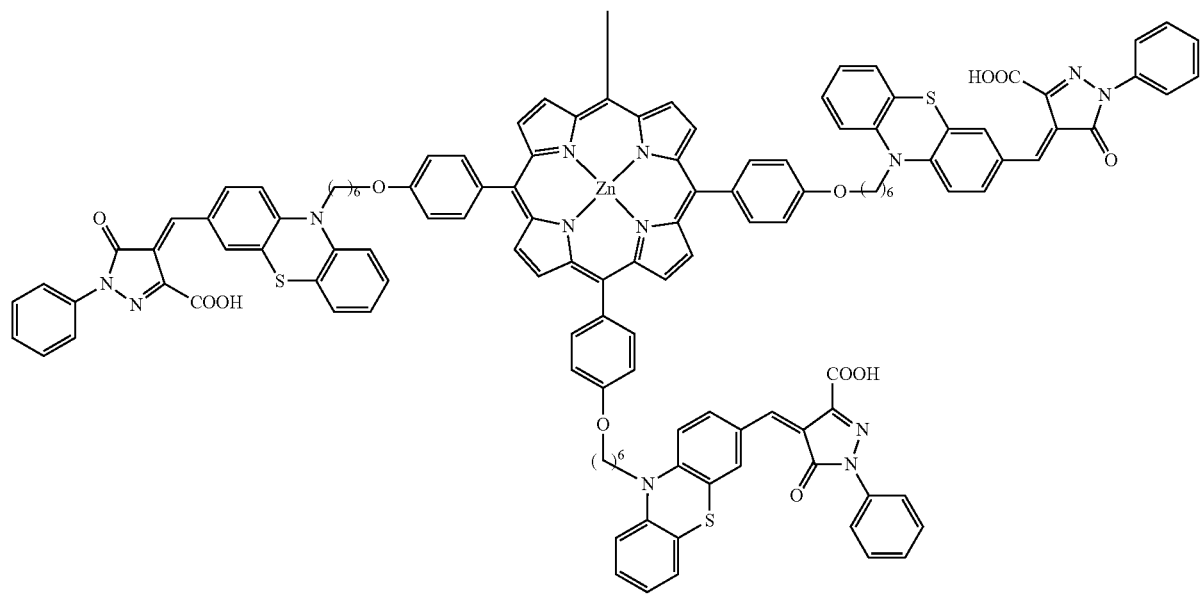
2-4
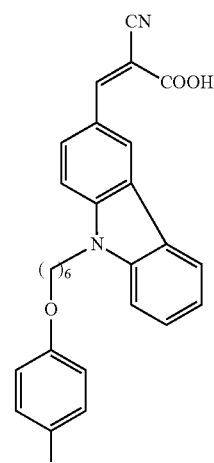

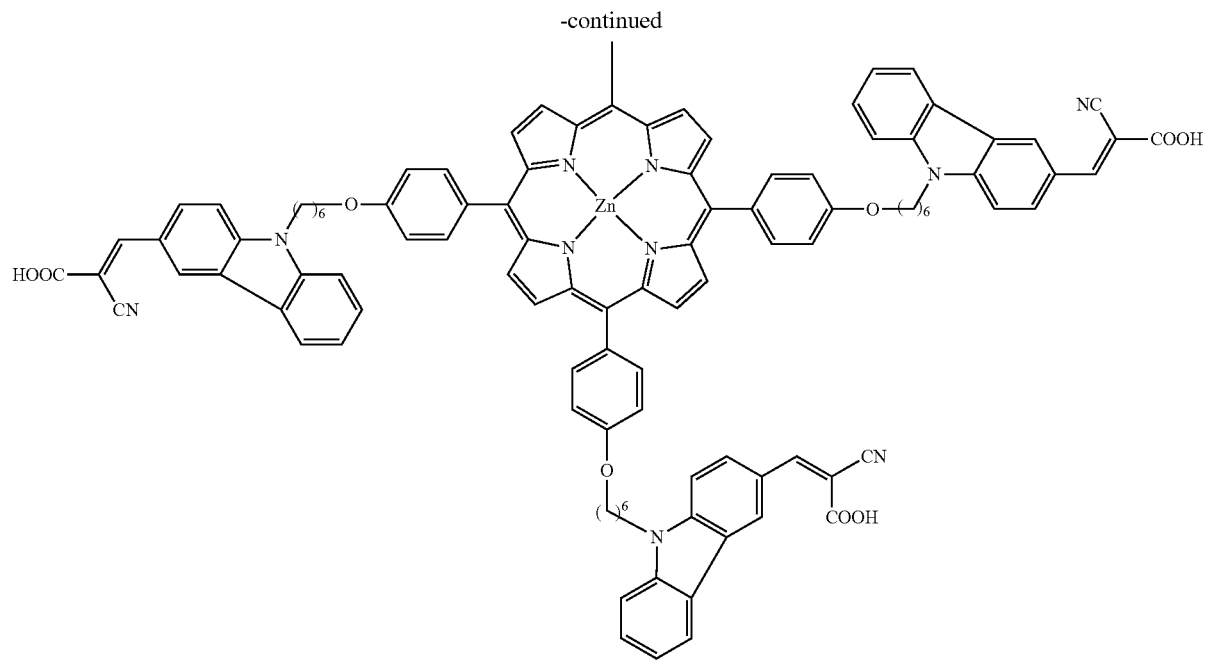
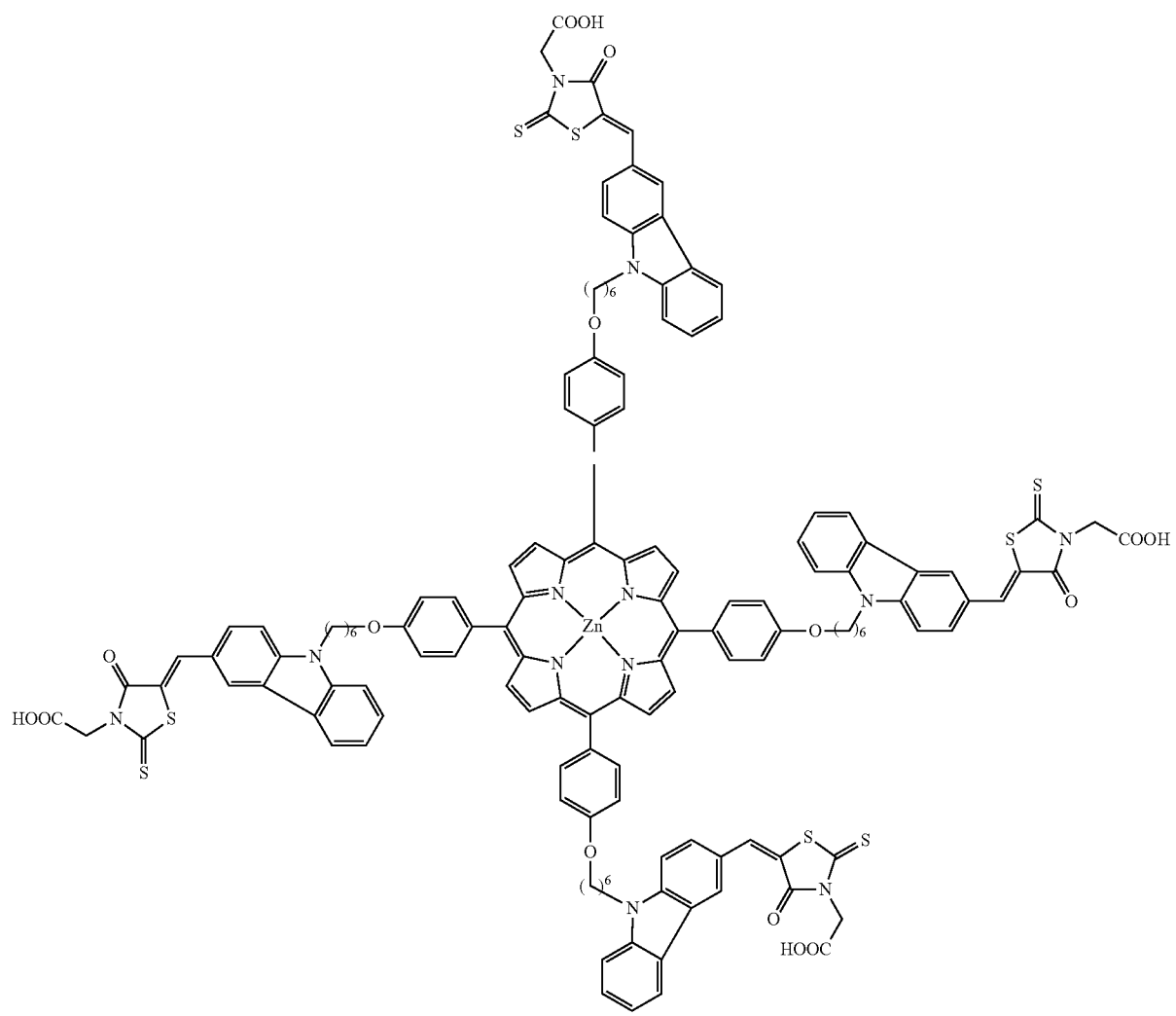
2-5

2-6
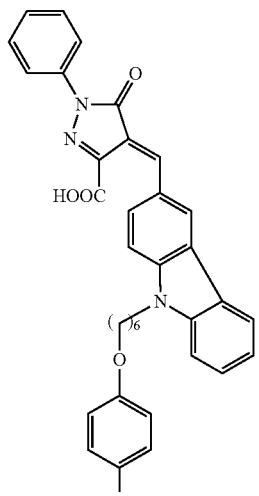
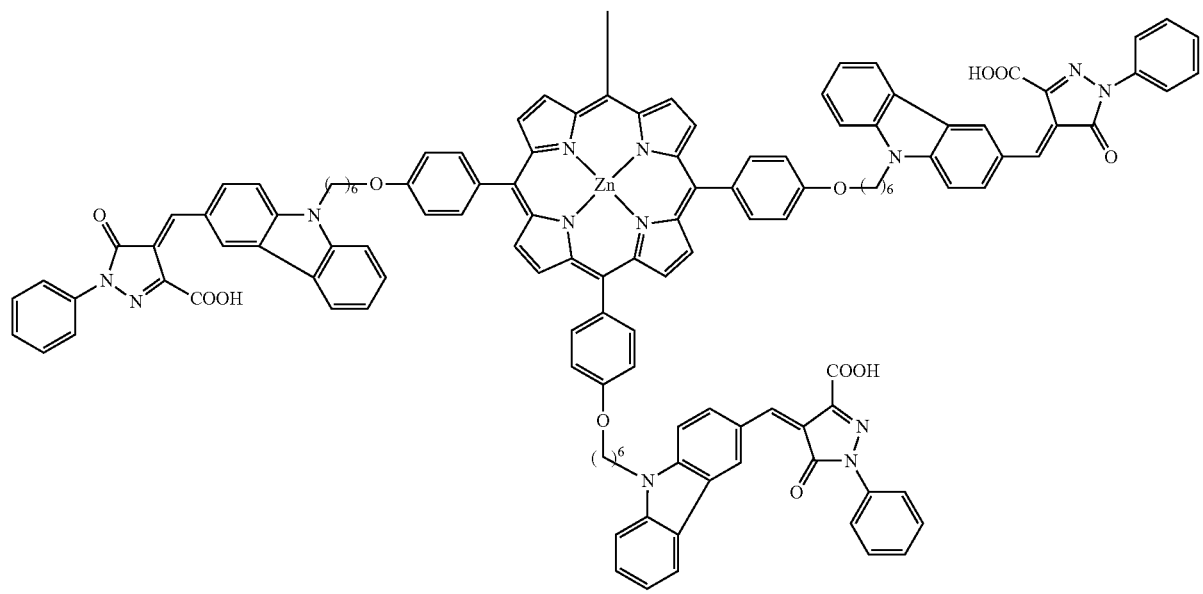
2-7
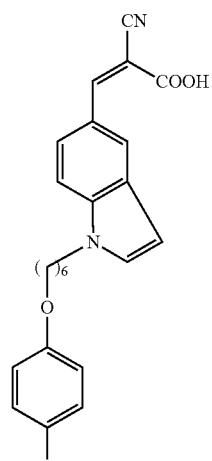

-continued
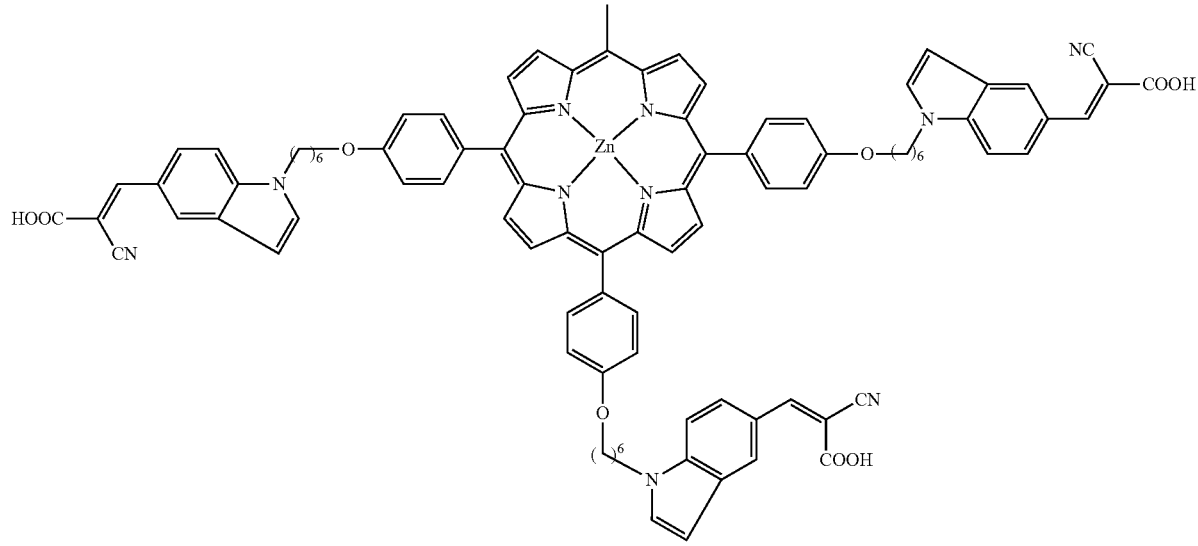
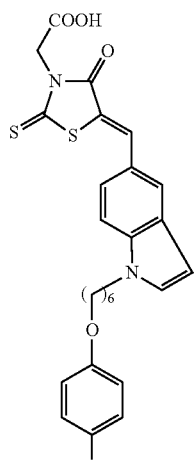
2-8
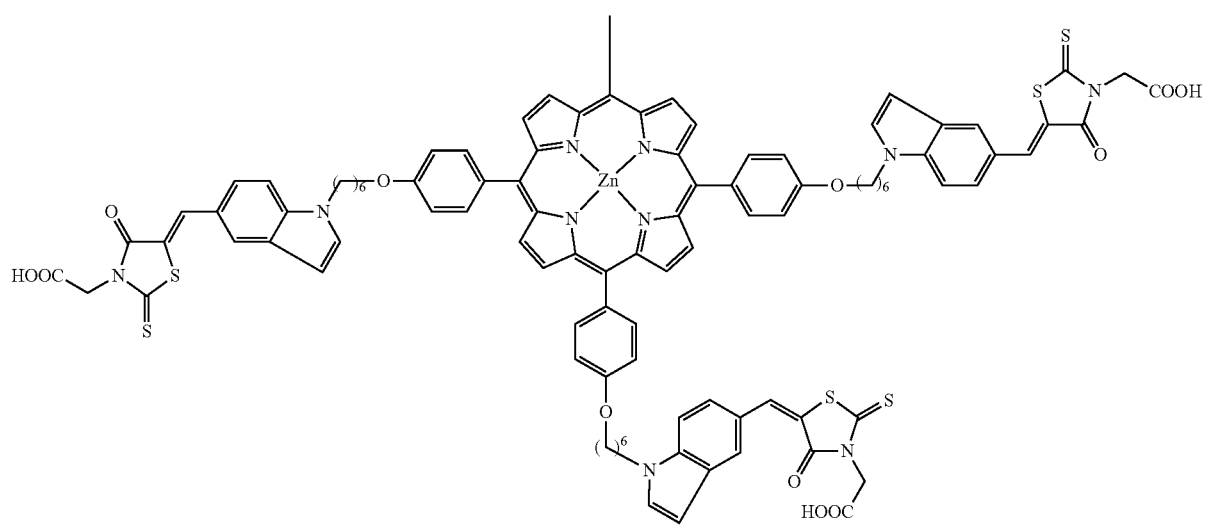

2-9
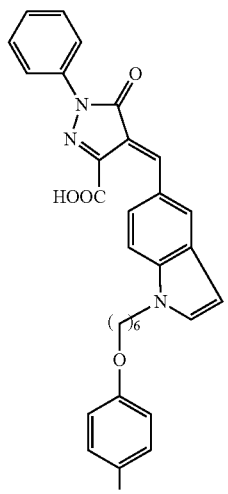
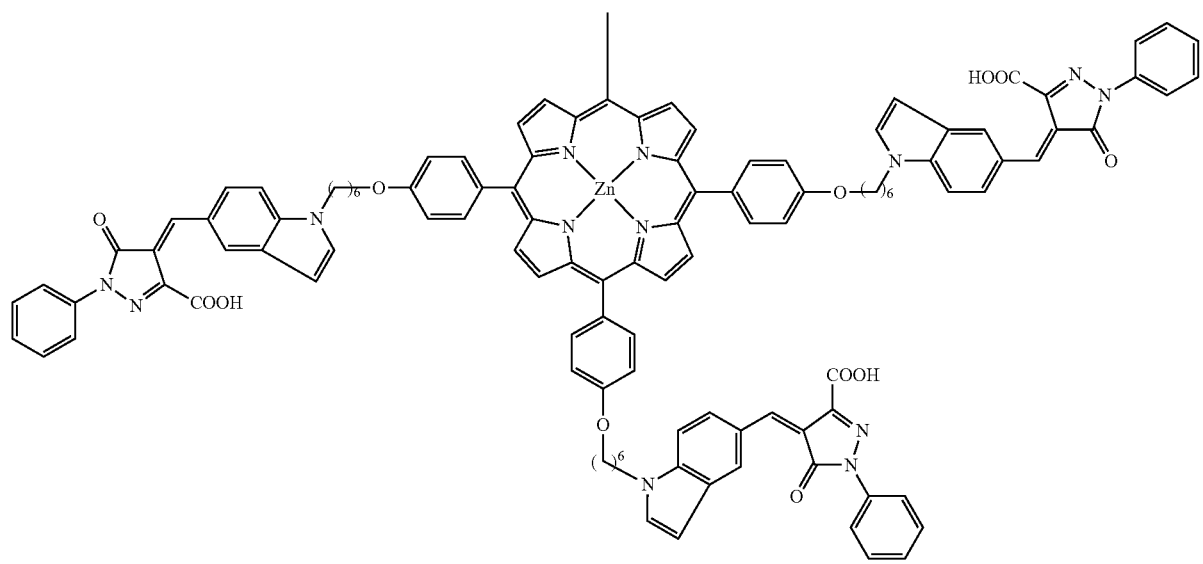
2-10
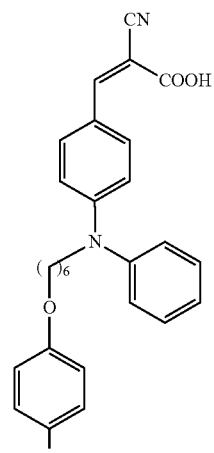

-continued
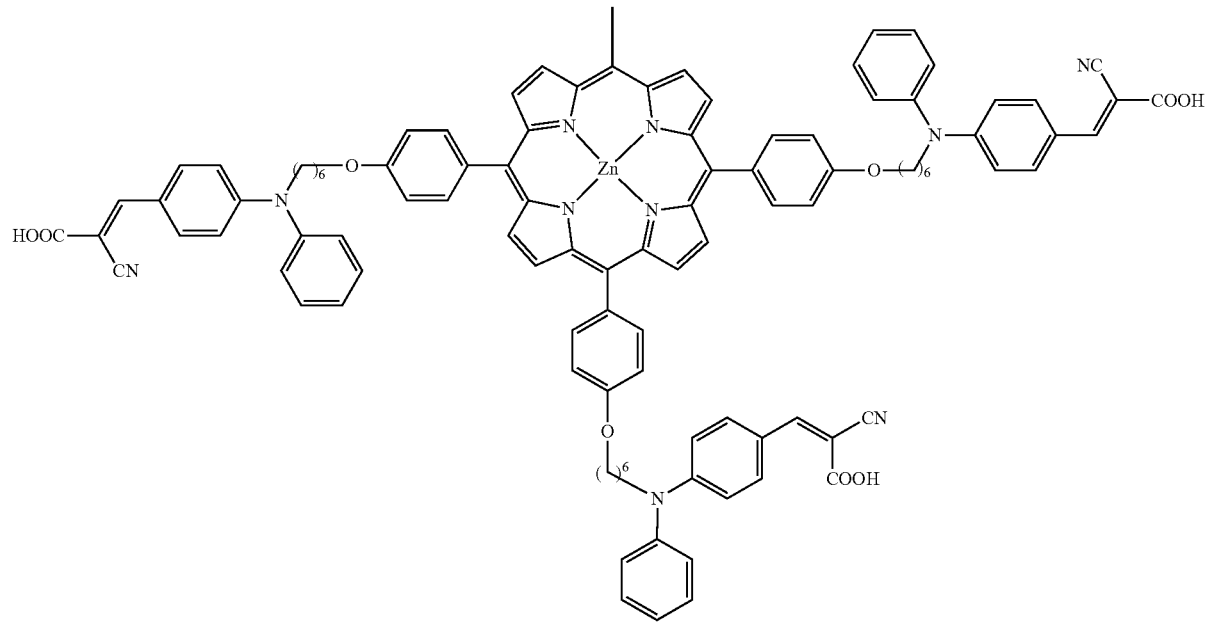
2-11
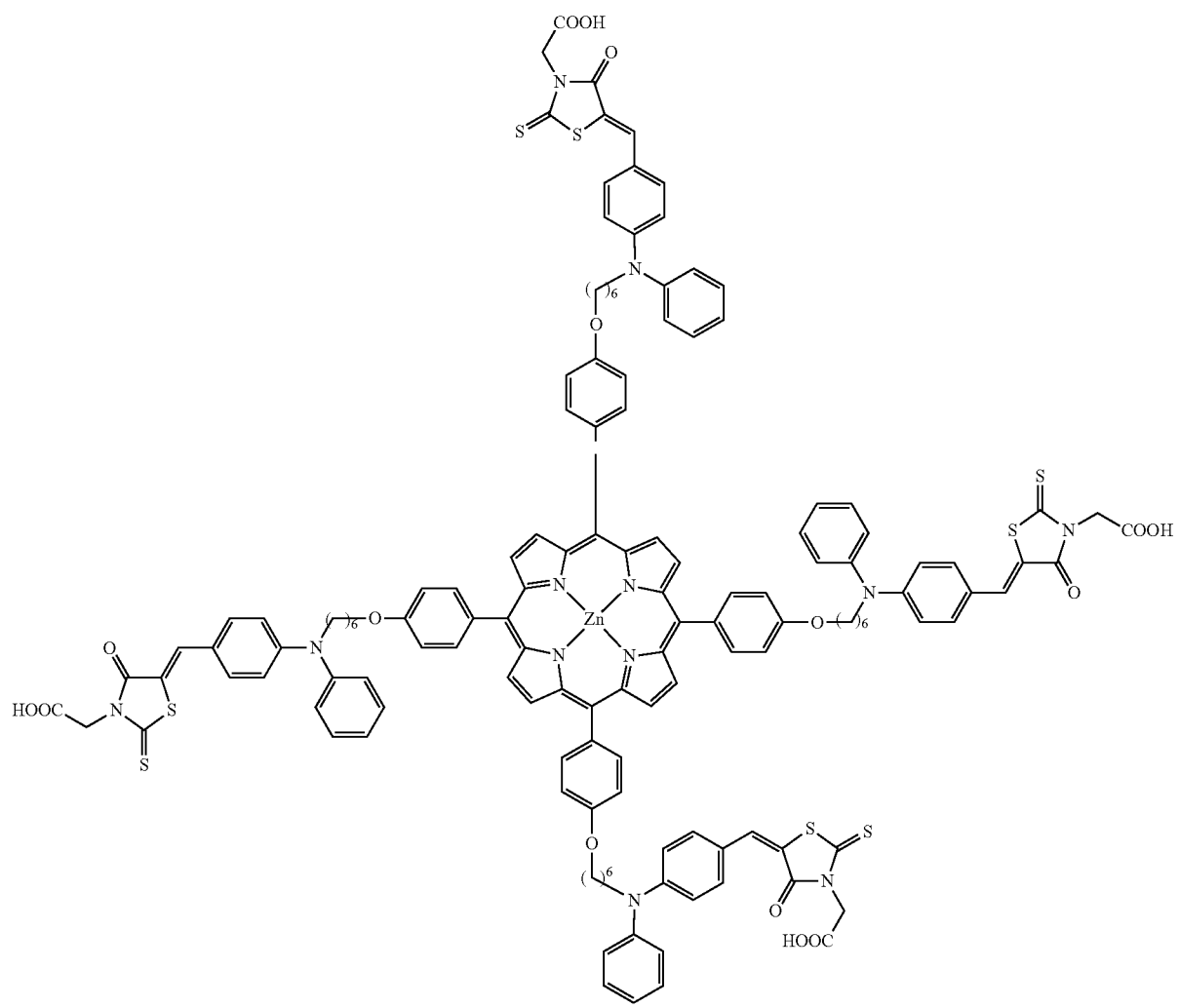

-continued 2-12

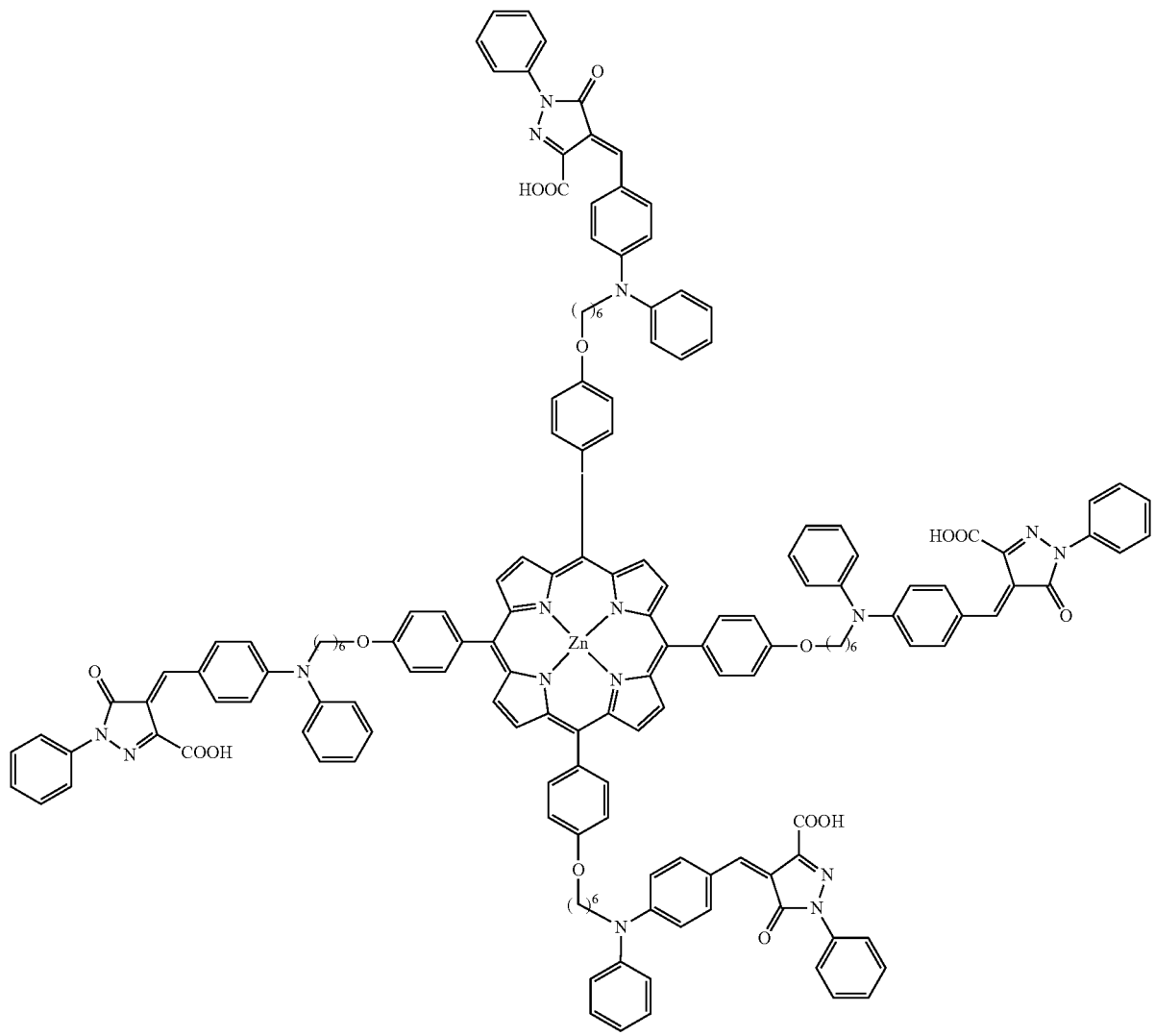

In addition, a dye-sensitized solar cell includes a first electrode; a second electrode; and a dye layer formed between the first electrode and the second electrode, wherein the dye layer includes at least one of organic dyes represented by Chemical Formula 1 or 2.

A better understanding of the present invention may be obtained via the following synthesis examples for organic dyes represented by Chemical Formula 1 or 2 in dye-sensitized solar cells, and fabrication examples for dye-sensitized solar cells, which are set forth to illustrate, but are not to be construed as limiting the present invention.

SYNTHESIS EXAMPLES

Synthesis Examples for the compounds of the invention are described below, and are merely illustrative, and the compounds may be prepared by a variety of methods other than the following methods.

1. Synthesis of Intermediate (1) Synthesis of 5,10,15,20-tert-(4-hydroxyphenyl)porphyrin <Scheme 1>

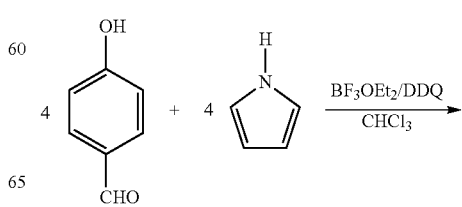

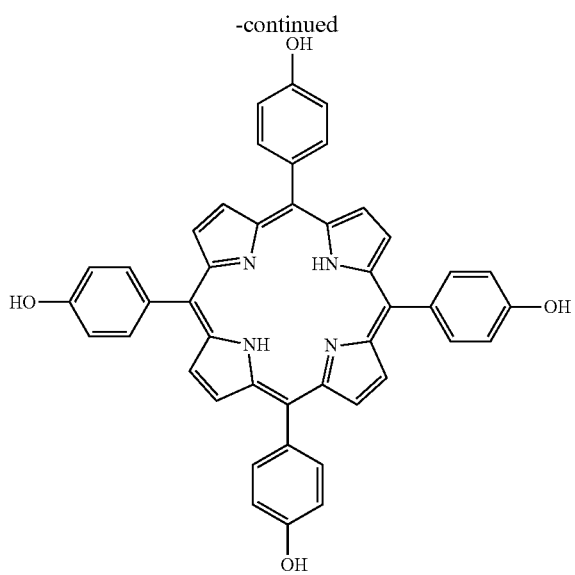

In a 1 L Erlenmeyer flask, pyrrole (2.32 mL, 33.49 mmol), 4-hydroxybenzaldehyde (5 mL, 35 mmol) and 1 L of $CHCl_3$ were placed and stirred at room temperature for 30 min. $BF_3OEt_2$ (Boron Trifluoride Diethyl Ether, 1.17 mL, 9.21 mmol) was added, and the resulting mixture was stirred at room temperature for 1 hr, after which DDQ (2,3-dichloro-5,6-dicyano-1,4-benzoquinone, 5.70 g, 25.12 mmol) was added, and the resulting mixture was stirred for hr. TLC and then filtration under reduced pressure were performed, and the solvent was removed from the obtained solution under reduced pressure, followed by separation using column chromatography and washing with cold ethanol, affording a product (yield: 15%).

$^1H$ NMR (400 MHz, $CDCl_3$): δ 8.78-8.86 (m, 8H), 8.46 (m, 8H), 8.27-8.15 (m, 8H) HR-MS (MARDI): $C_{44}H_{30}N_4O_4$ m/z: 678.2 $[M+H]^+$ (2) Synthesis of [5,10,15,20-tert-(4-hydroxyphenyl)porphyrin]Zn <Scheme 2>

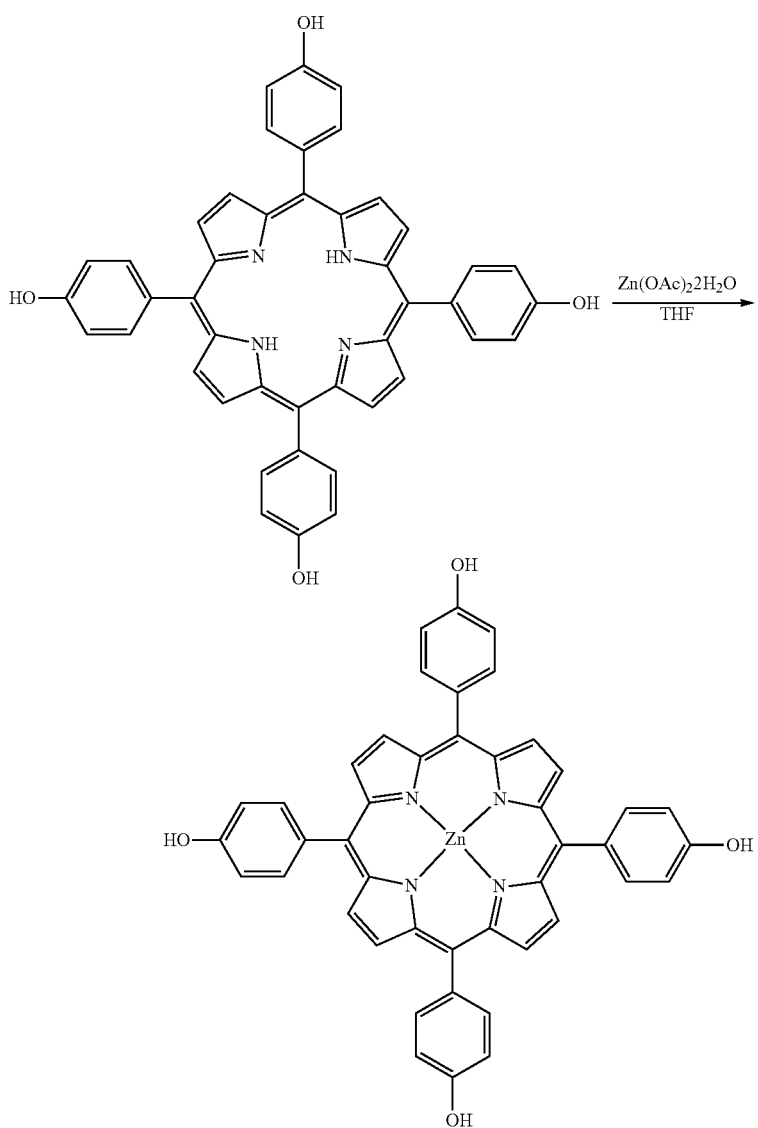

5,10,15,20-tert-(4-hydroxyphenyl)porphyrin (0.5 g, 0.525 mmol) obtained in Scheme 1, zinc acetate dihydrate (0.577 g, 2.63 mmol), and 50 mL of THF were placed and the resulting mixture was stirred under reflux for one day. After completion of the reaction, the reaction product was cooled to room temperature, extracted with CHCl$_3$ and washed several times with a sodium bicarbonate aqueous solution and water. The organic layer was dried with anhydrous sodium sulfate, and the solvent was removed under reduced pressure, followed by washing with cold ethanol and drying in a vacuum, affording a product (yield: 90%).

$^1$H NMR (300 MHz, DMSO-d$_6$): δ 8.96-8.88 (m, 8H), 8.42-8.39 (d, 2H), 8.3-8.28 (d, 2H), 8.2-8.17 (d, 6H), 7.80-7.78 (d, 6H), HR-MS (MARDI): C$_{45}$H$_{31}$N$_4$O$_4$Zn m/z: 752.2 [M+H]$^+$ (3) Synthesis of 10-(6-bromo-hexyl)-10H-phenothiazine <Scheme 3>

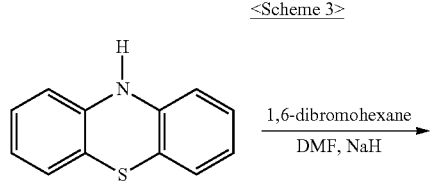

1,6-dibromohexane
DMF, NaH

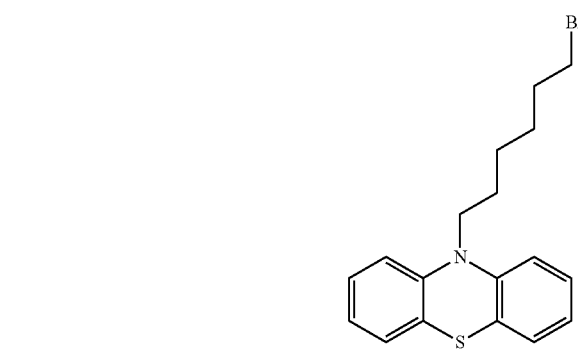

Phenothiazine (5.0 g, 0.025 mol) and 1,6-dibromohexane (10.0 g, 0.065 mol) were dissolved in 100 mL of DMF (dimethyl formamide), and NaOH (sodium hydride, 0.98 g, 0.041 mol) was slowly added at room temperature. The resulting mixture was stirred at room temperature for 8 hr. After completion of the reaction, work-up was implemented in a solvent mixture of water and CHCl$_3$ at 1:1. Thereafter, the organic layer was separated using an extraction method, and the solvent was removed under reduced pressure, followed by silica gel column chromatography (chloroform:hexane, 1:5), affording a transparent liquid product (4.5 g, 49.7%).

$^1$H NMR (300 MHz, CDCl$_3$): δ 7.13 (d, J=5.1 Hz, 2H), 7.09 (d, J=7.5 Hz, 2H), 6.98 (d, J=7.2 Hz, 2H), 6.82 (d, J=8.1 Hz, 2H), 3.84 (t, J=6.9 Hz, 2H), 3.33 (t, J=6.6 Hz, 2H), 1.87-1.76 (m, 4H), 1.47-1.40 (m, 4H). HR-MS (MARDI): C$_{18}$H$_{20}$BrNS m/z: 363.15 [M+H]$^+$ (4) Synthesis of 10-(6-bromo-hexyl)-10H-phenothiazine-3-carbaldehyde <Scheme 4>

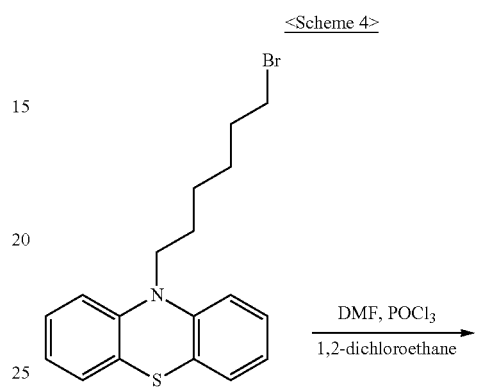

DMF, POCl$_3$
1,2-dichloroethane

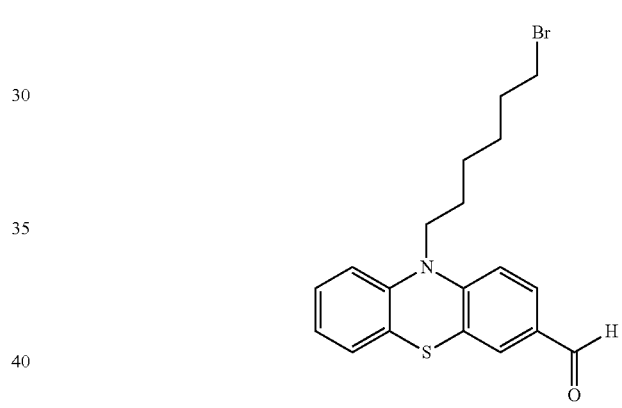

10-(6-bromohexyl)-10H-phenothiazine (4.5 g, 12.4 mmol) obtained as above was dissolved in 20 mL of 1,2-dichloroethane, DMF (10.88 g, 0.15 mol) was added, and POCl$_3$ (phosphorus oxychloride, 7.6 g, 50.0 mmol) was slowly added dropwise at 0° C., and the resulting mixture was stirred under reflux for 8 hr.

After completion of the reaction, work-up was implemented in a solvent mixture of water and CHCl$_3$ at 1:1. Thereafter, the organic layer was separated using an extraction method, and the solvent was removed under reduced pressure, followed by silica gel column chromatography (chloroform:hexane, 1:3), affording a yellow solid product (2.5 g, 51.6%).

$^1$H NMR (300 MHz, CDCl$_3$): δ 9.78 (s, 1H), 7.63 (d, J=8.7 Hz, 1H), 7.59 (s, 1H), 7.17 (d, J=7.2 Hz, 1H), 7.12 (d, J=8.7 Hz, 1H), 6.97 (d, J=7.5 Hz, 1H), 6.92 (d, J=9.9 Hz, 1H), 6.87 (d, J=7.5 Hz, 1H), 3.90 (t, J=7.2 Hz, 2H), 3.49 (t, J=6.3 Hz, 2H), 1.82-1.79 (m, 4H), 1.45 (m, 4H). HR-MS (MARDI): C$_{19}$H$_2$OBrNOS m/z: 390.3 [M+H]$^+$ (5) Synthesis of 5,10,15,20-tert-[4-hydroxyphenyl (10-hexyl-10H-phenothiazine-3-carbaldehyde)]porphyrin

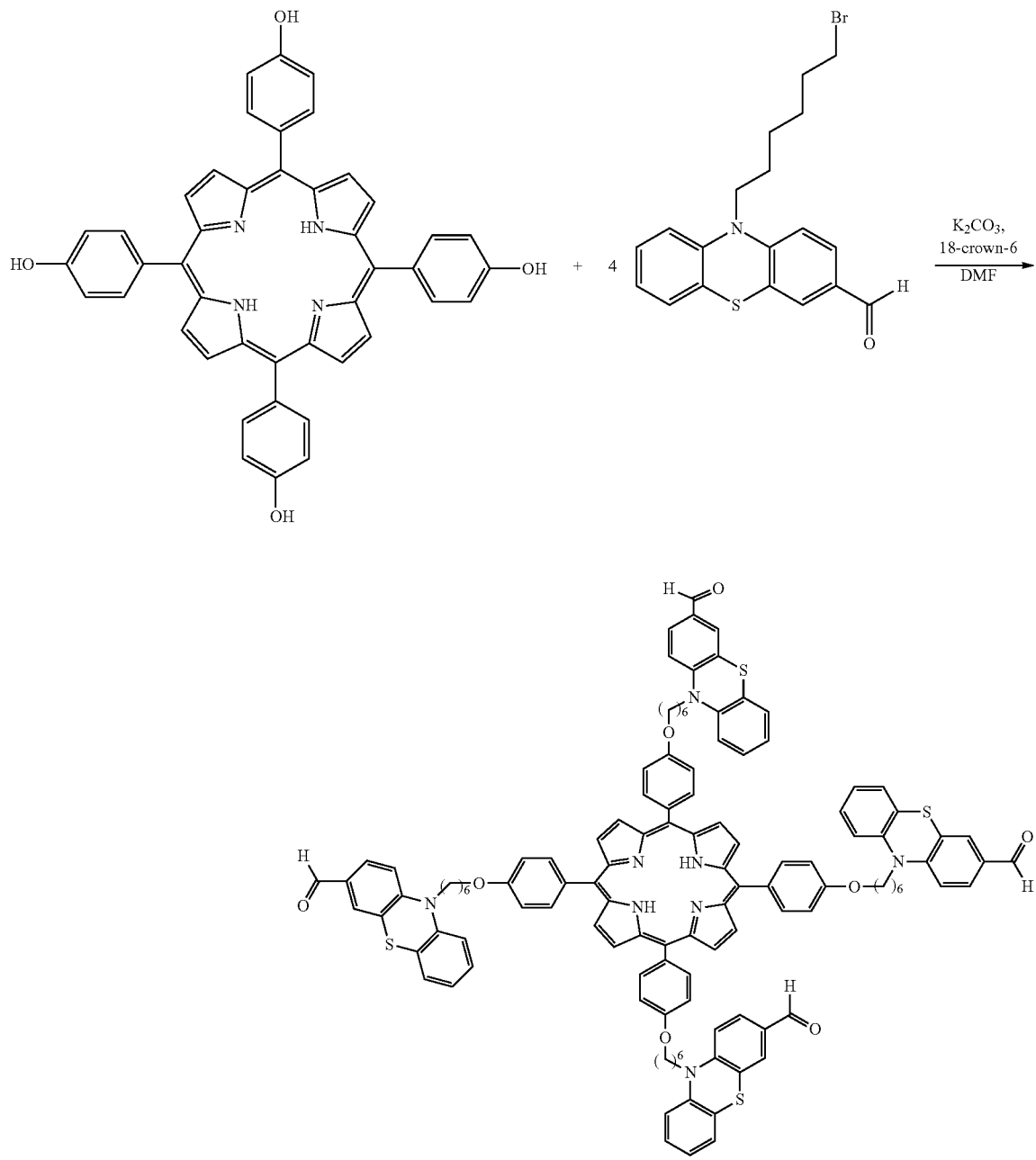

10-(6-bromo-hexyl)-10H-phenothiazine-3-carbaldehyde (2.5 g, 9.0 mmol) obtained as above, 5,10,15,20-tert-(4-hydroxyphenyl)porphyrin (0.64 g, 2.1 mmol) and $K_2CO_3$ (4.15 g, 12.8 mmol) were dissolved in 20 mL of DMF, a small amount of 18-crown-6 was added, and the resulting mixture was stirred under reflux at 110° C. for 24 hr. After completion of the reaction, work-up was implemented in a solvent mixture of water and $CHCl_3$ at 1:1. Thereafter, the organic layer was separated using an extraction method, and the solvent was removed under reduced pressure, followed by silica gel column chromatography (ethylacetate:chloroform, 1:10), affording a dark-blue solid product (1.3 g, 50.1%).

$^1$H NMR (300 MHz, $CDCl_3$): δ 9.87 (s, 4H), 8.32 (d, 8H), 7.96 (d, 8H), 7.64-7.2 (m, 28H), 6.95-6.28 (d. 12H), 3.89 (m, 12H), 2.09 (s, 3H), 1.84-1.75 (m, 12H), 1.49 (m, 12H). HR-MS (MARDI): $C_{100}H_{66}N_8O_8S_4$ m/z: 1635 $[M+H]^+$

2. Synthesis of Compound of Chemical Formula 1
(1) Synthesis of Compound 1-1 [4-hydroxyphenyl (10-hexyl-10H-phenothiazine)]porphyrin)
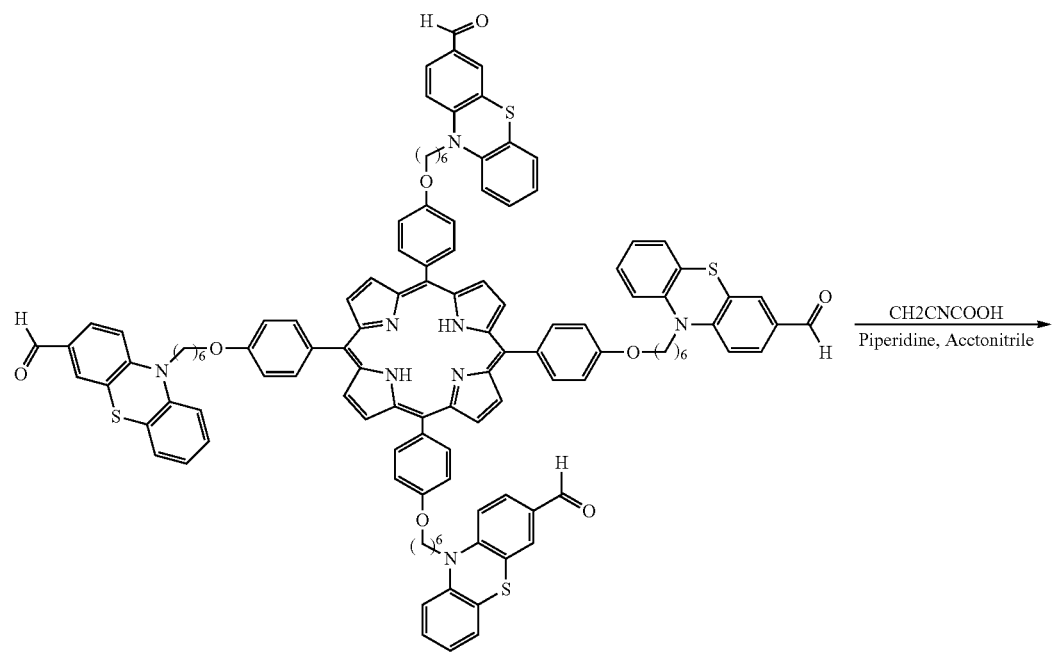
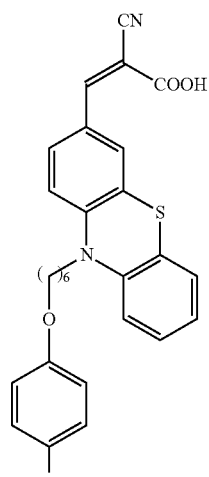

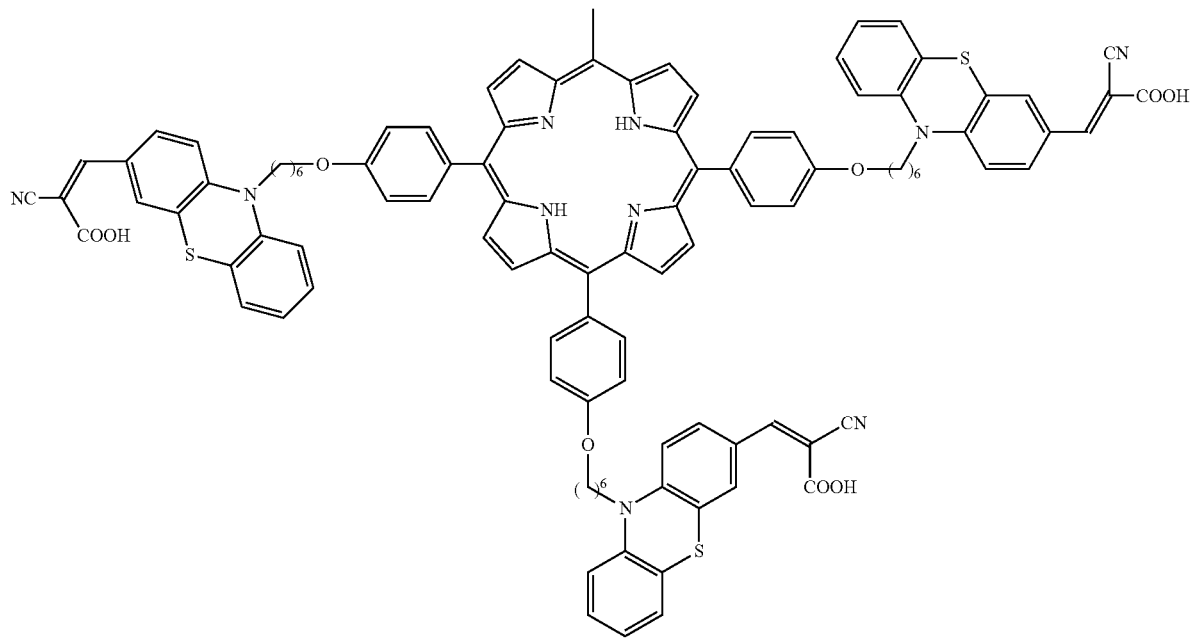

5,10,15,20-tert-[4-hydroxyphenyl(10-hexyl-10H-phenothiazine-3-carbaldehyde)]porphyrin (1.3 g, 1.05 mmol) obtained as above, piperidine (0.40 g, 5.25 mmol) and cyanoacetic acid (0.45 g, 5.25 mmol) were dissolved in 50 mL of acetonitrile, and the resulting mixture was stirred under reflux for 6 hr. After completion of the reaction, the produced solid in the reactor was filtered, affording a blue solid product (0.8 g, 53.3%).

$^1$H NMR (300 MHz, DMSO-$d_6$): δ 8.39 (s, 4H), 8.02 (d, 8H), 8.0 (d, 8H), 7.62-7.1 (m, 28H), 6.95-6.28 (d. 12H), 3.89 (m, 12H), 2.09 (s, 3H), 1.84-1.75 (m, 12H), 1.49 (m, 12H)

HR-MS (MARDI): $C_{113}H_{73}N_{12}O_{12}S_4S_4$ m/z: 1983.6 [M+H]$^+$ (2) Synthesis of Compound 1-4 (5,10,15,20-tert-[4-hydroxyphenyl(10-hexyl-10H-carbazole)]porphyrin)

The same procedures as in Schemes 1 and 3 to 6 were performed, with the exception that 9H-carbazole was used as the starting material in Scheme 3. After completion of the reaction, the produced solid in the reactor was filtered, affording a blue solid product.

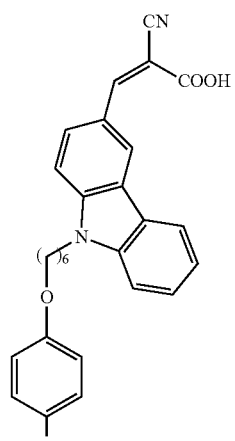

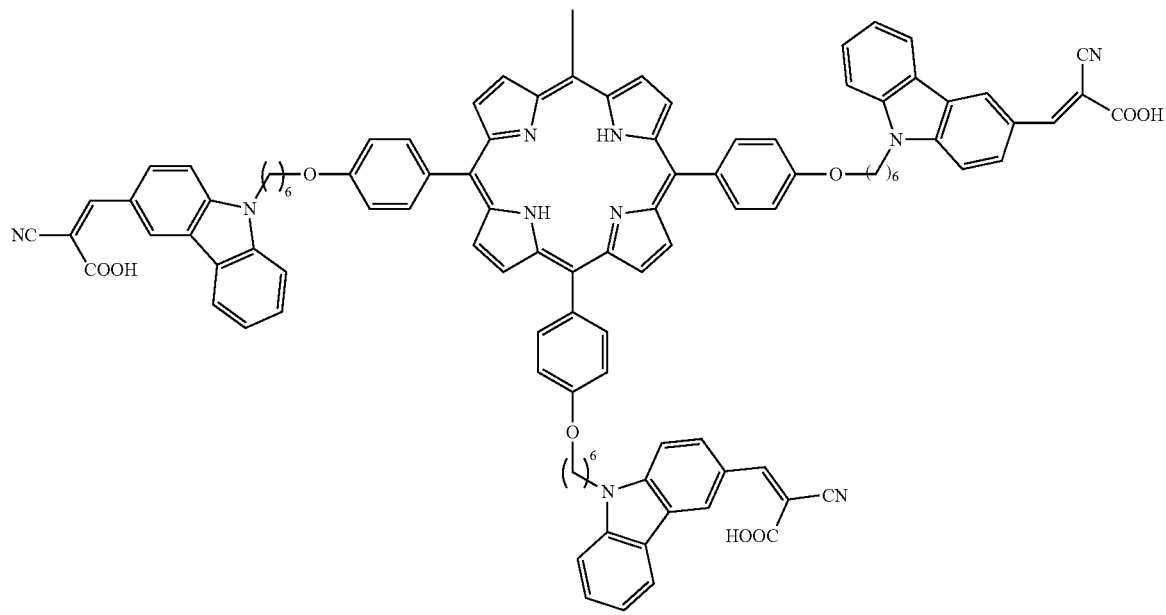

$^1$H NMR (300 MHz, DMSO-$d_6$): δ 8.26 (s, 4H), 7.85 (d, 12H), 7.65-7.45 (d, 28H), 6.95-6.28 (d. 12H), 3.89 (m, 12H), 2.09 (s, 3H), 1.84-1.75 (m, 12H), 1.49 (m, 12H) HR-MS (MARDI): $C_{112}H_{70}N_{12}O_{12}$ m/z: 1774.59 [M+H]$^+$

3. Synthesis of compound of Chemical Formula 2

(1) Synthesis of Compound 2-1 (5,10,15,20-tert-[4-hydroxyphenyl(10-hexyl-10H-Phenothiazine)porphyrin]Zn)

The compound obtained by Scheme 2 was subjected to the same procedures as in Schemes 3 to 6. After completion of the reaction, the produced solid in the reactor was filtered, affording a violet solid product.

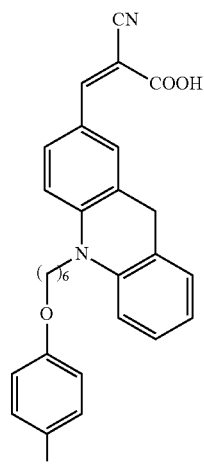

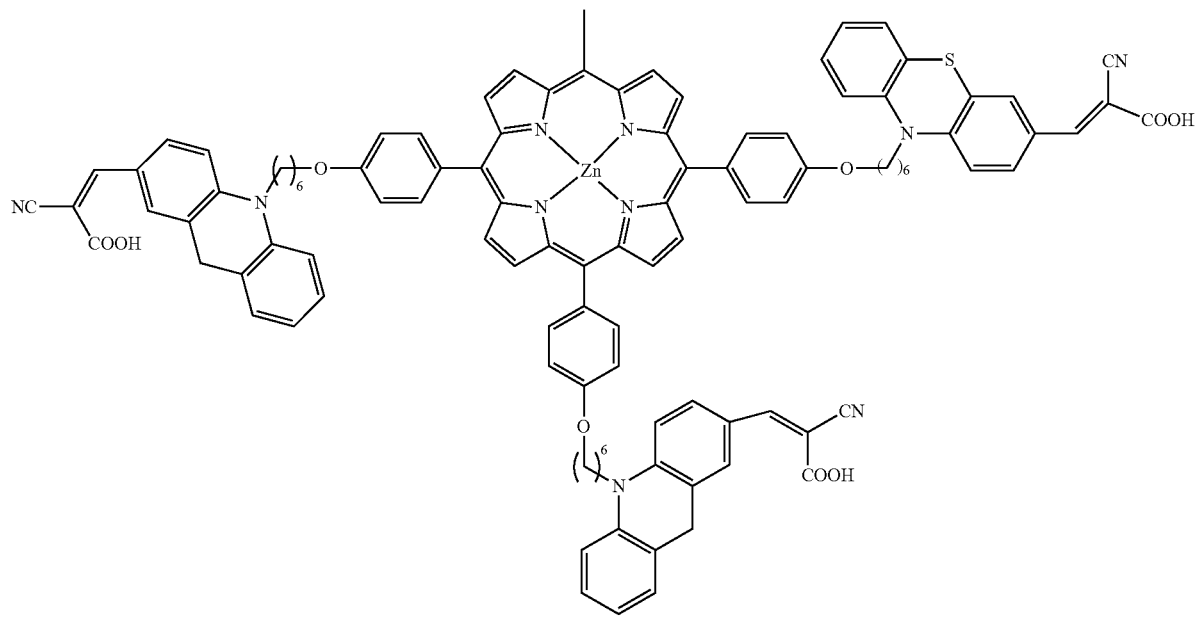

$^1$H NMR (300 MHz, DMSO-d$_6$): δ 8.69 (s, 4H), 8.32 (d, 8H), 8.1-7.99 (d, 8H), 7.72-7.25 (m, 28H), 6.95-6.28 (d, 12H), 3.89 (m, 12H), 2.09 (s, 3H), 1.84-1.75 (m, 12H), 1.49 (m, 12H) HR-MS (MARDI): C$_{113}$H$_{71}$N$_{12}$O$_{12}$S$_4$Zn m/z: 1979 [M+H]$^+$ (2) Synthesis of Compound 2-4 (5,10,15,20-tert-[4-hydroxyphenyl(10-hexyl-10H-carbazole)porphyrin] Zn)

The compound obtained by Scheme 2 was subjected to the same procedures as in Schemes 3 to 6, with the exception that 9H-carbazole was used as the starting material in Scheme 3. After completion of the reaction, the produced solid in the reactor was filtered, affording a blue solid product.

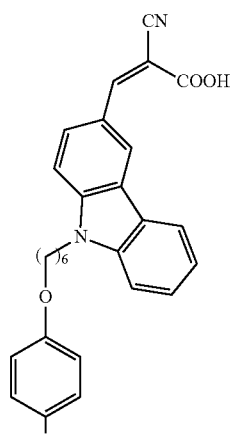

-continued

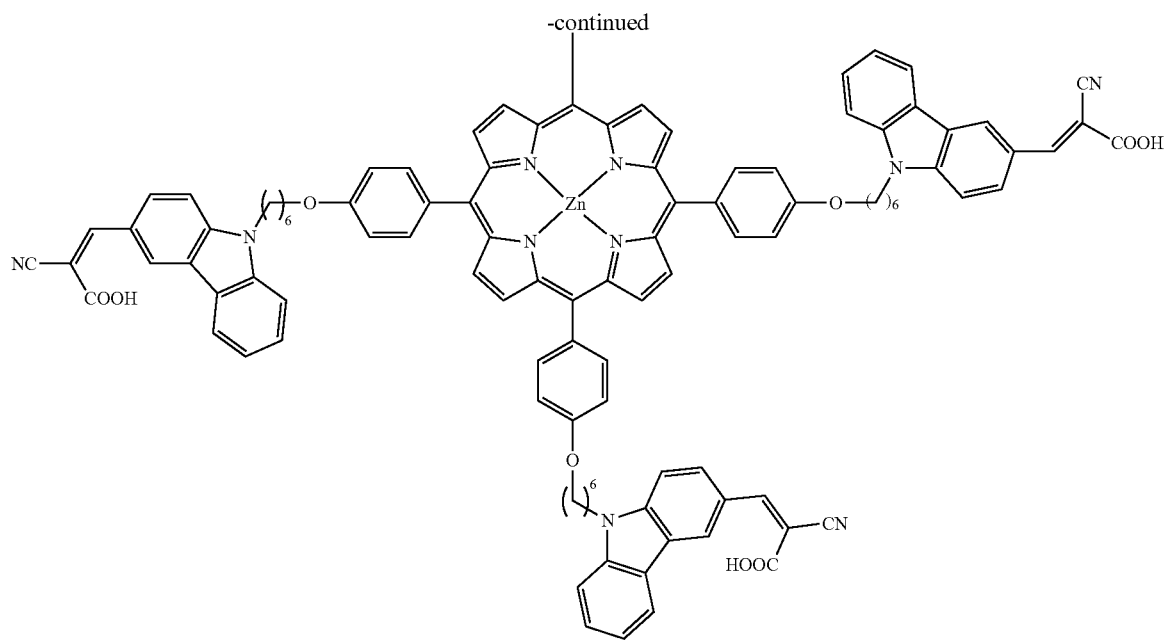

¹H NMR (300 MHz, DMSO-d₆): δ 8.19 (s, 4H), 8.07 (d, 12H), 7.59-7.45 (d, 28H), 6.85-6.28 (d. 12H), 4.1 (m, 12H), 3.09 (s, 3H), 1.84-1.75 (m, 12H), 1.49 (m, 12H) HR-MS (MARDI): $C_{113}H_{71}N_{12}O_{12}Zn$ m/z: 1846.64 $[M+H]^+$

FD-MS values of Compounds 1-1 to 1-12 and 2-1 to 2-12 according to the present invention prepared in the above synthesis examples are given in Table 1 below.

TABLE 1

| Compound | FD-MS | Compound | FD-MS |
|---|---|---|---|
| 1-1 | m/z = 1903.41 | 1-2 | m/z = 2327.23 |
| 1-3 | m/z = 2379.56 | 1-4 | m/z = 1775.52 |
| 1-5 | m/z = 2199.34 | 1-6 | m/z = 2251.67 |
| 1-7 | m/z = 1759.53 | 1-8 | m/z = 2007.34 |
| 1-9 | m/z = 2059.67 | 1-10 | m/z = 1767.59 |
| 1-11 | m/z = 2207.41 | 1-12 | m/z = 2259.73 |
| 2-1 | m/z = 1980.35 | 2-2 | m/z = 2404.17 |
| 2-3 | m/z = 2456.50 | 2-4 | m/z = 1852.46 |
| 2-5 | m/z = 2276.28 | 2-6 | m/z = 2328.61 |
| 2-7 | m/z = 1759.53 | 2-8 | m/z = 2084.28 |
| 2-9 | m/z = 2136.61 | 2-10 | m/z = 1844.53 |
| 2-11 | m/z = 2284.35 | 2-12 | m/z = 2336.67 |

Evaluation of Fabrication of Dye-sensitized Solar Cell

Experimental Example 1

Fabrication of Dye-sensitized Solar Cell

A conductive glass substrate (FTO; TEC8, Pilkington, 8 $\Omega cm^2$, Thickness of 2.3 mm) was cleaned in ethanol using ultrasonic waves. A commercial $TiO_2$ paste (20 nm, Solar-nonix) was prepared, applied on the cleaned glass substrate using a doctor blade, and then burned at 500° C. for 30 min. The thickness of the burned $TiO_2$ paste layer was measured by an Alpha-step IQ surface profiler (KLA Tencor).

To use another $TiO_2$ paste as a scattering layer, the burned layer was coated again with $TiO_2$ particles having a size of 400 nm, and then burned at 500° C. for 30 min. The prepared $TiO_2$ film was immersed in a 0.04 M $TiCl_4$ aqueous solution at 70° C. for 30 min.

For dye adsorption, the annealed $TiO_2$ electrode was immersed in a dye solution comprising 0.3 mM Compound 1-1 at 50° C. for 3 hr. A thin film formed from a 0.7 mM $H_2PtCl_6$ solution dissolved in 2-propanol was subjected to thermal reduction at 400° C. for 20 min, thus preparing a Pt counter electrode.

The dye-adsorbed $TiO_2$ electrode and the Pt counter electrode were assembled using, as a binder, 60 μm thick Surlyn (Dupont 1702). A liquid electrolyte was placed by means of a through hole of the counter electrode. The electrolyte was composed of 3-propyl-1-methyl-imidazolium iodide (PMII, 0.7 M), lithium iodide (LiI, 0.2 M), iodine ($I_2$, 0.05 M), and t-butylpyridine (TBP, 0.5 M) dissolved in acetonitrile/valeronitrile (85:15).

Experimental Example 2

Fabrication of Dye-sensitized Solar Cell

A dye-sensitized solar cell was fabricated in the same manner as in Experimental Example 1, with the exception of using Compound 1-4 according to the present invention as the dye.

Comparative Example

A dye-sensitized solar cell was fabricated in the same manner as in Experimental Example 1, with the exception of using the following comparative compound as the dye (Japanese Patent Publication Application No. 2002-063949).

Comparative Compound

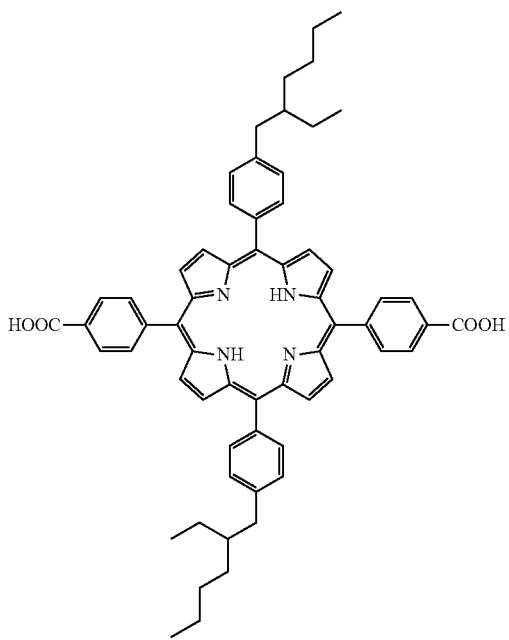 [SMILES: CCCCC(CC)Cc1ccc(-c2c3nc(c(-c4ccc(C(=O)O)cc4)c4ccc([nH]4)c(-c4ccc(CC(CC)CCCC)cc4)c4nc(c(-c5ccc(C(=O)O)cc5)c5ccc2[nH]5)C=C4)C=C3)cc1]

The results of measurement of the properties of the dye-sensitized solar cells thus fabricated are given in Table 2 below, wherein the measurement condition of the electric properties using a solar simulator is AM 1.5 (1 sun, 100 mW/cm$^2$).

TABLE 2

| | Dye | Voc (V) | Jsc (mAcm$^{-2}$) | FF (%) | η (%) |
|---|---|---|---|---|---|
| Exp. Ex. 1 | Compound 1-1 | 0.65 | 7.32 | 67.0 | 3.21 |
| Exp. Ex. 2 | Compound 1-4 | 0.63 | 5.53 | 67.10 | 2.28 |
| Comp. Ex | Comparative Compound | 0.54 | 3.30 | 59.47 | 1.04 |

In Table 2, Jsc is the short-circuit photocurrent density, Voc is the open-circuit photovoltage, FF is the fill factor, and η is the total photoelectric conversion efficiency. As such, performance of the dye-sensitized solar cell was measured over the work area of 0.24 cm$^2$.

Meanwhile, FIG. 1 is a graph illustrating the current-voltage properties of the dye-sensitized solar cells including the compounds of the invention, and Table 2 is made with reference to FIG. 1.

As is apparent from Table 2 and FIG. 1, in the case where phenyl and ether are sequentially connected to the porphyrin core and then the electron donor such as phenothiazine is linked with the alkyl group as in the present invention, intermolecular recombination may be prevented, ultimately improving both Voc (open voltage) and Jsc (short-circuit current) compared to Comparative Example. The quality of the solar cell is determined by FF and light efficiency. When the compound according to the present invention is used as the organic dye, FF becomes much higher compared to when using the comparative compound, and as well, superior light efficiency may result.

Figure 2:
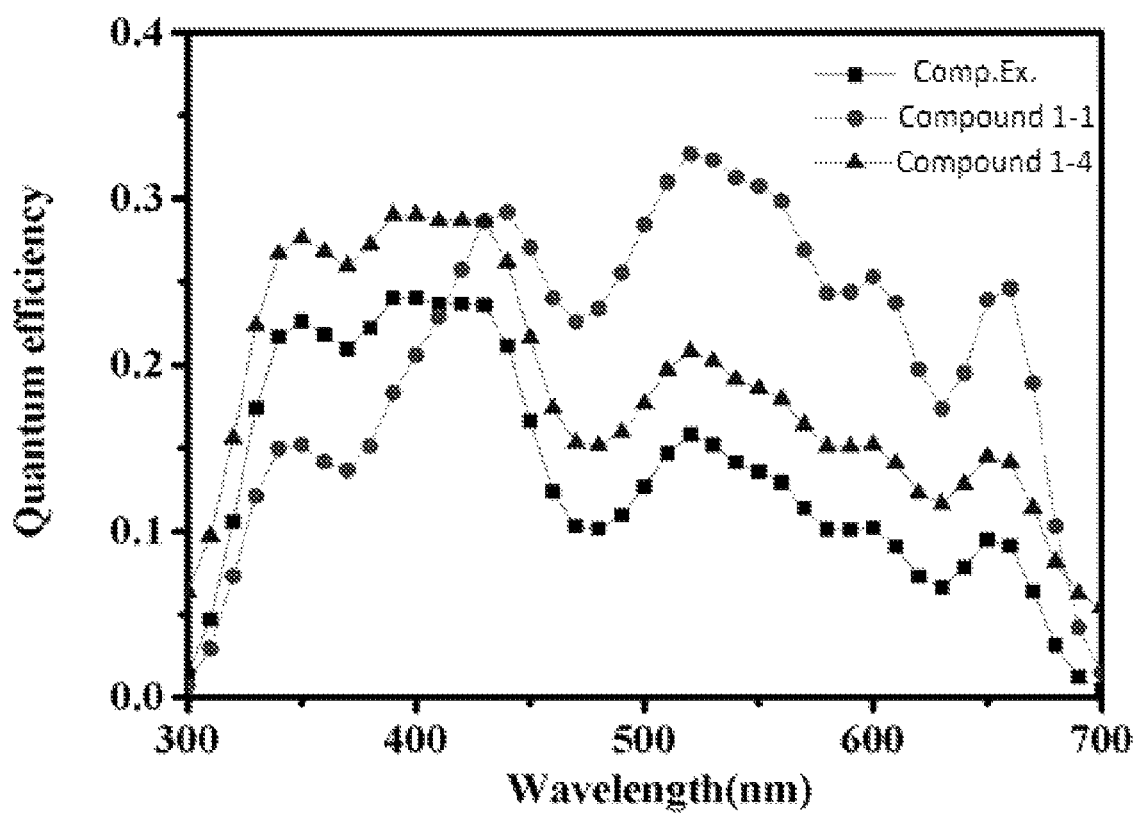
FIG. 2 is a graph illustrating a light absorption spectrum of an organic dye according to an embodiment of the present invention.

FIG. 2 is a graph illustrating light absorption spectrum of the dye including the compound according to an embodiment of the present invention. When using the compound according to the present invention, quantum efficiency depending on the wavelength is increased, compared to Comparative Example, and also, the use of a strong electron donor phenothiazine (Compound 1-1) results in shift to a long wavelength to thus absorb a wide wavelength range.

As described hereinbefore, the present invention provides a porphyrin-based compound, a dye including the same and a dye-sensitized solar cell. According to the present invention, a porphyrin compound which is easily synthesized and has high photoelectric conversion efficiency can be provided, by introducing a variety of substituents to a porphyrin derivative.

Also, according to the present invention, a dye for a dye-sensitized solar cell and a dye-sensitized solar cell using the same can be provided, wherein the use of a porphyrin derivative, having high planarity and able to prevent conversion from an excited state into a ground state, can prevent recombination of electrons to an electrolyte from porphyrin in an excited state, and the flow direction of electrons can be adjusted, thereby maximizing photoelectric conversion efficiency.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A compound represented by any one of Chemical Formulas 1 and 2 below:

<Chemical Formula 1>

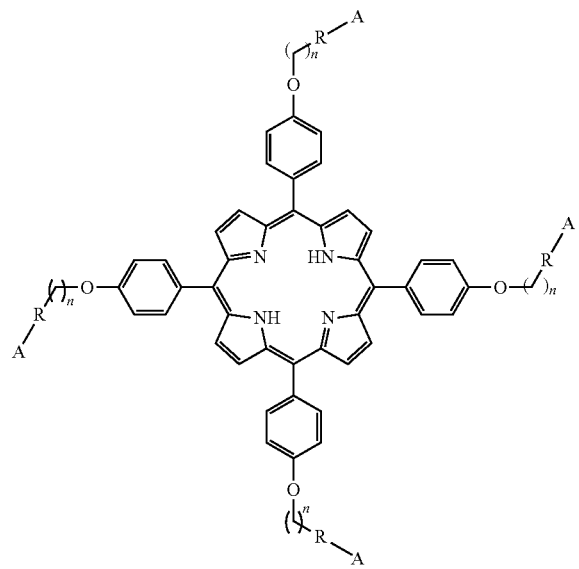

-continued

<Chemical Formula 2>

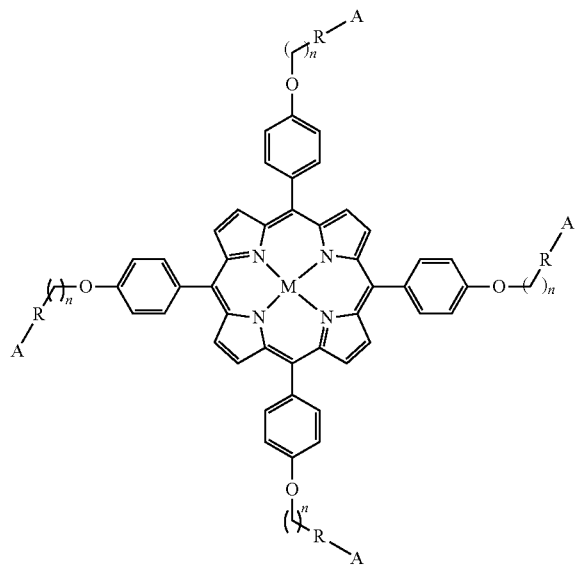

wherein M is Zn or Pt; and n is independently an integer of 1 to 20,

R is independently selected from the group consisting of a $C_6$-$C_{60}$ arylene group, a fluorenylene group, a $C_2$-$C_{60}$ heterocyclic group containing at least one heteroatom of O, N, S, Si and P, and A is independently selected from the group consisting of

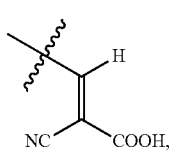 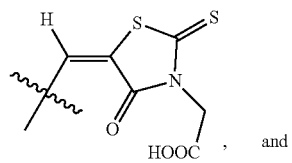

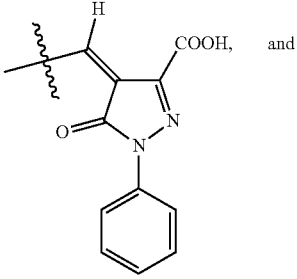

each of the heterocyclic group, the arylene group, and the fluorenylene group is optionally further substituted with one or more substituents selected from the group consisting of a carboxyl group, a hydroxyl group, halogen, a silane group, a boron group, a cyano group, a nitro group, an aryl group or a heterocyclic-substituted amine group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_6$-$C_{20}$ aryl group, a $C_2$-$C_{20}$ heterocyclic group, a $C_3$-$C_{20}$ cycloalkyl group, a $C_7$-$C_{20}$ arylalkyl group and a $C_8$-$C_{20}$ arylalkenyl group.

2. The compound of claim 1, wherein R is selected from the group consisting of the following:

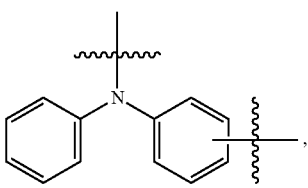

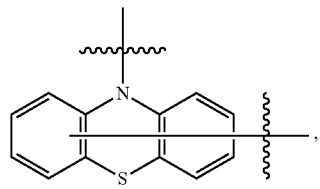

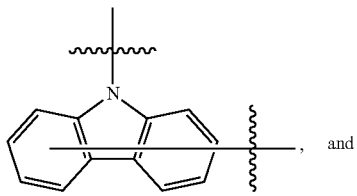

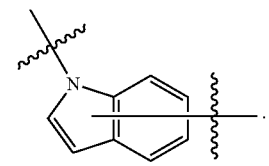

3. The compound of claim 1, wherein the compound is represented by Chemical Formula 1.

4. The compound of claim 3, wherein the compound represented by Chemical Formula 1 is any one of the following compounds:

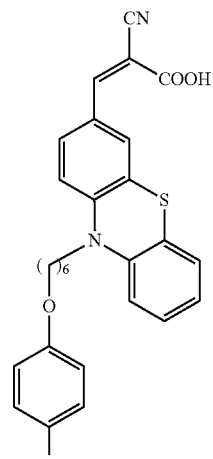
1-1
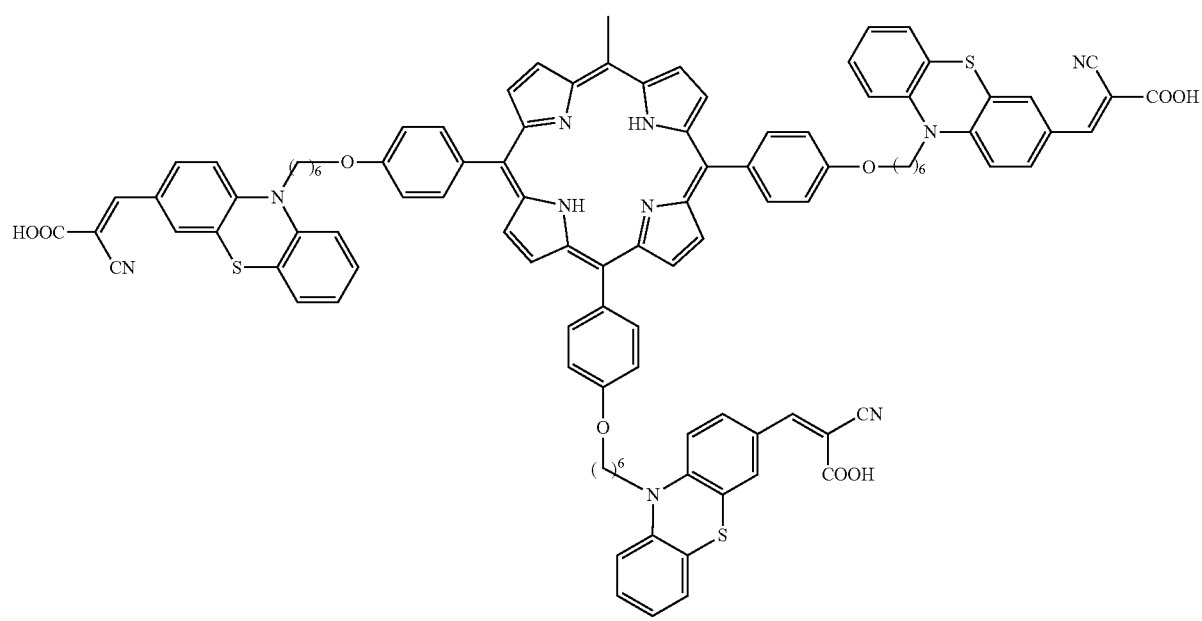
1-2
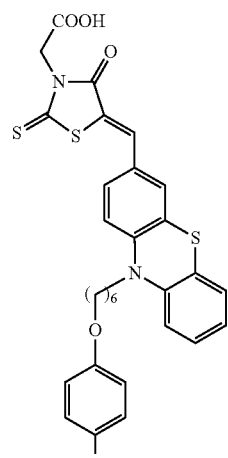

-continued
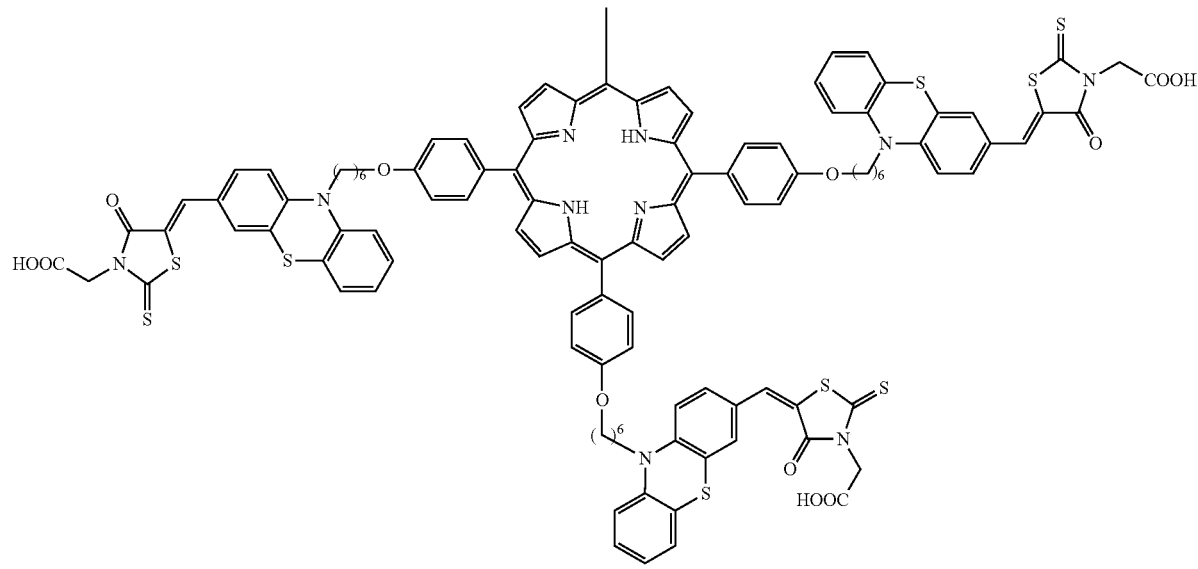
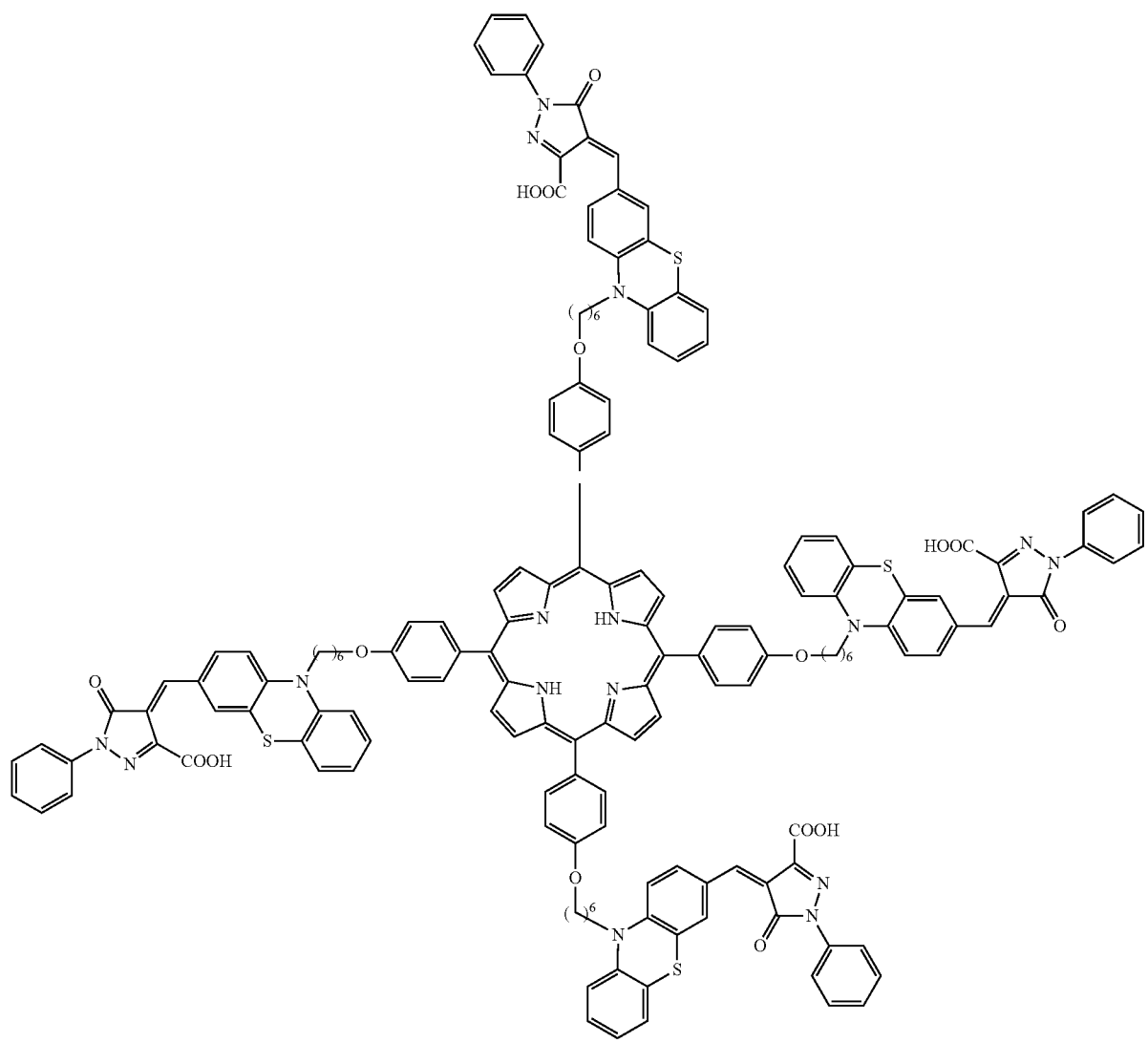
1-3

1-4
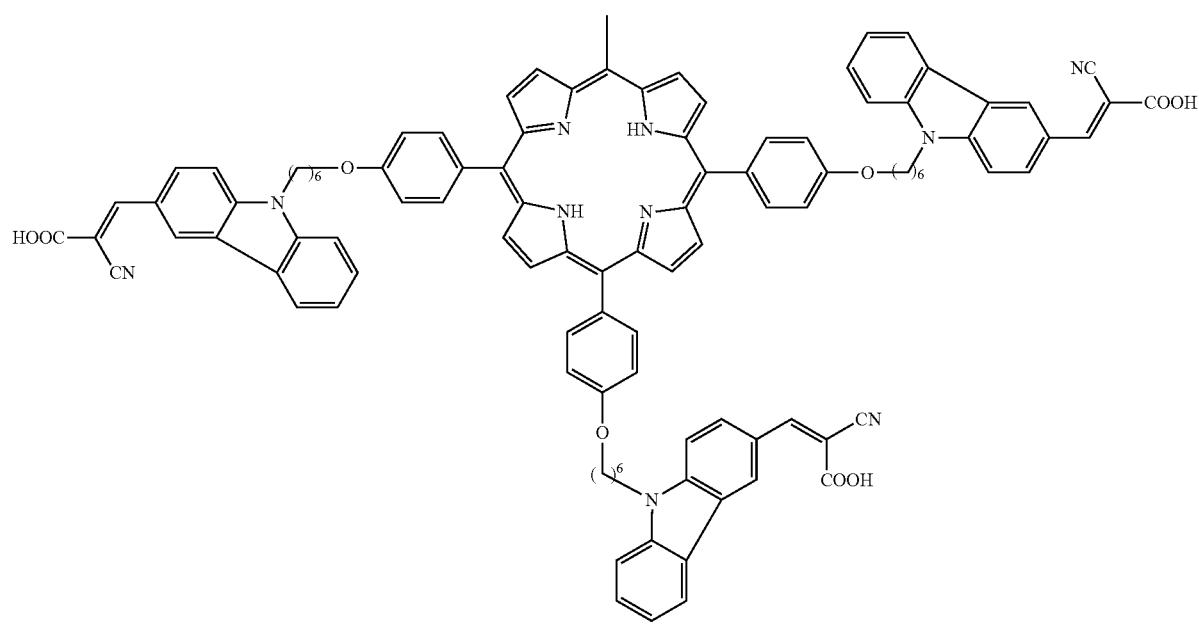
1-5
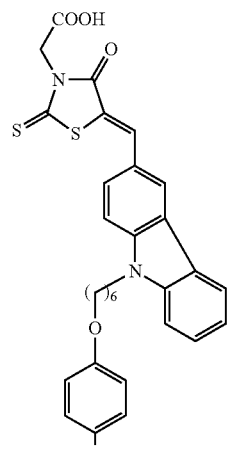

67
68
-continued
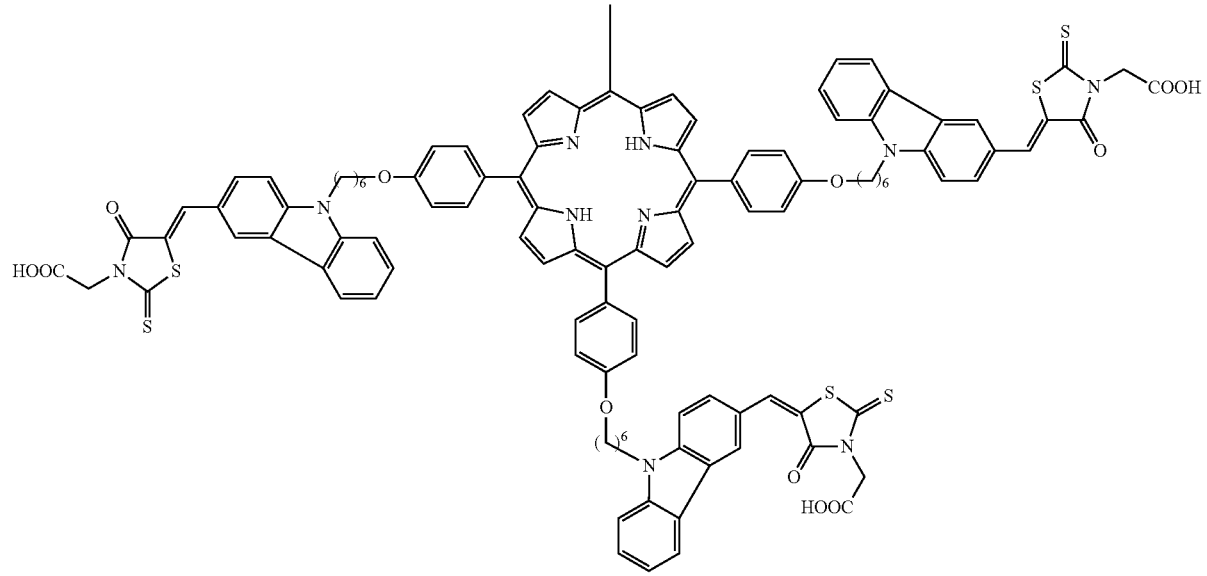
1-6
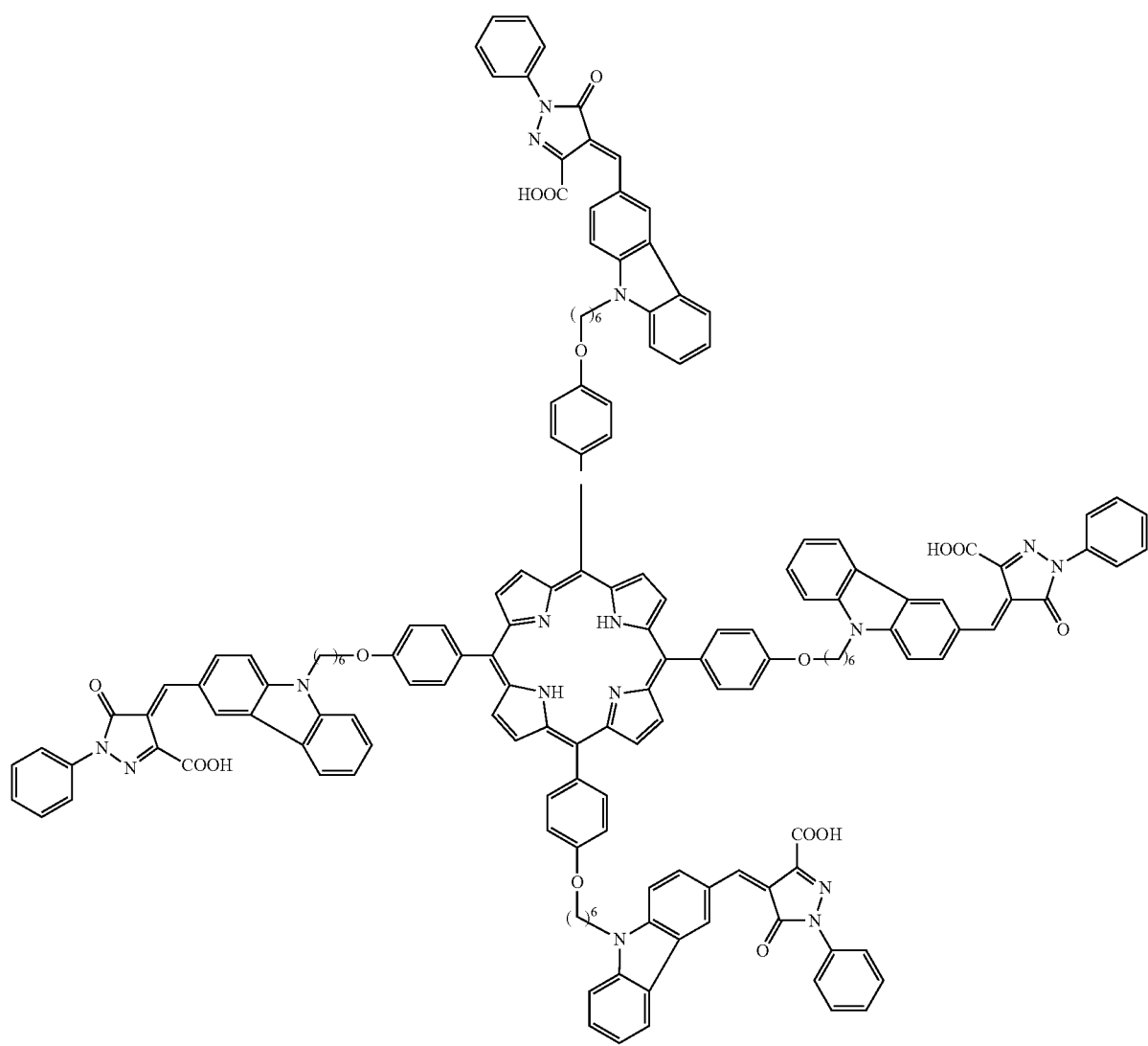

1-7
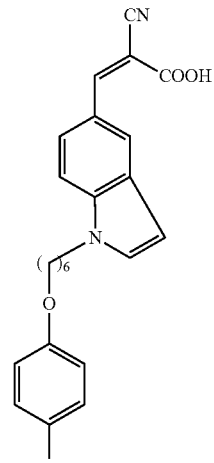
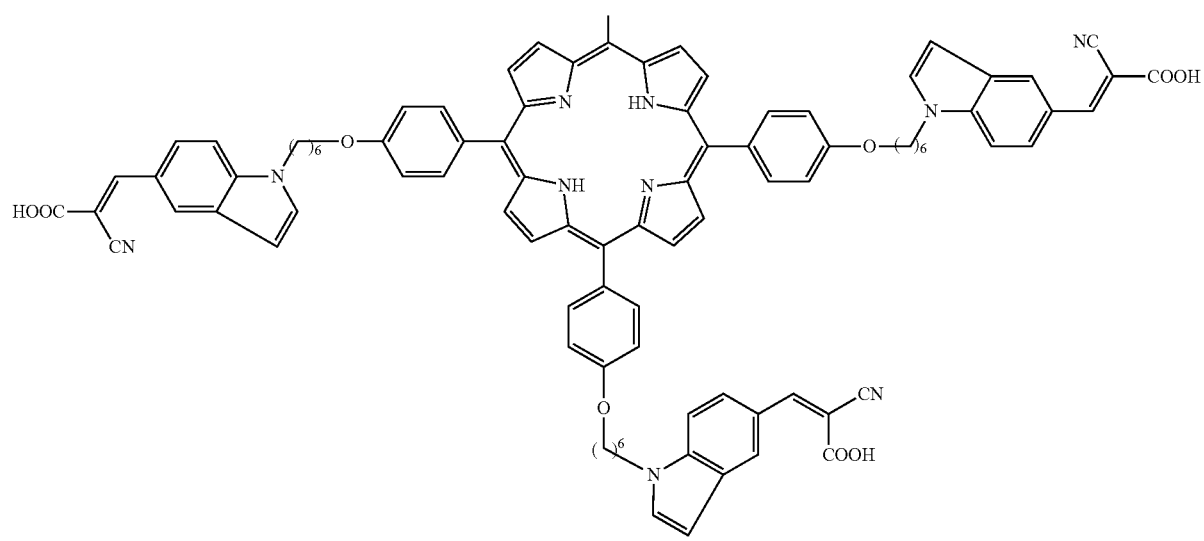
1-8
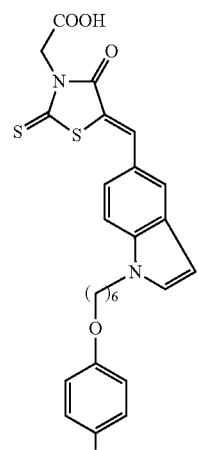

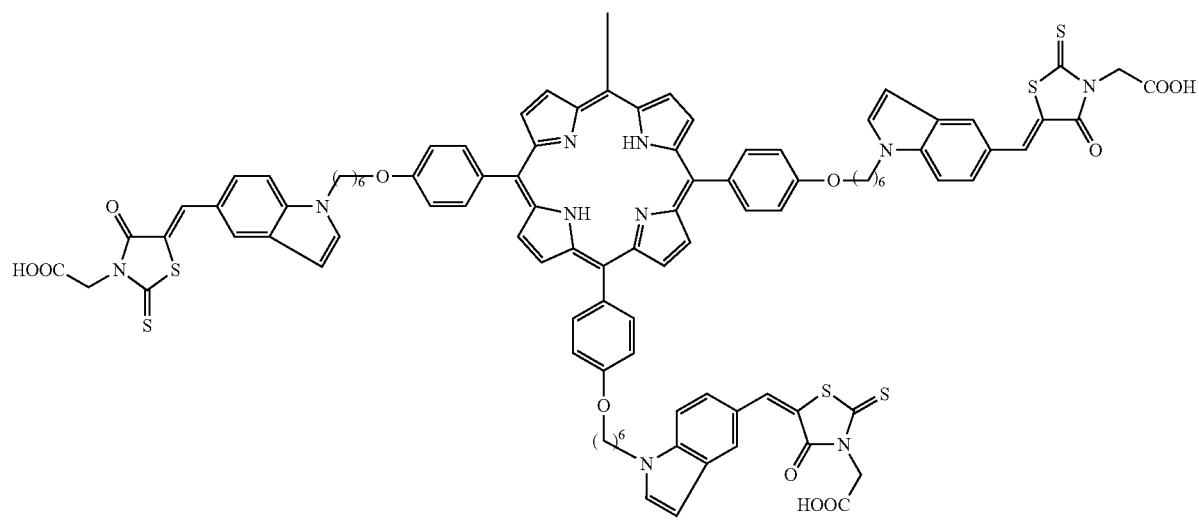
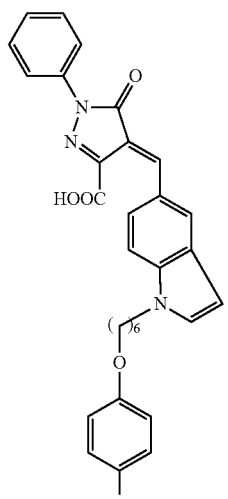
1-9
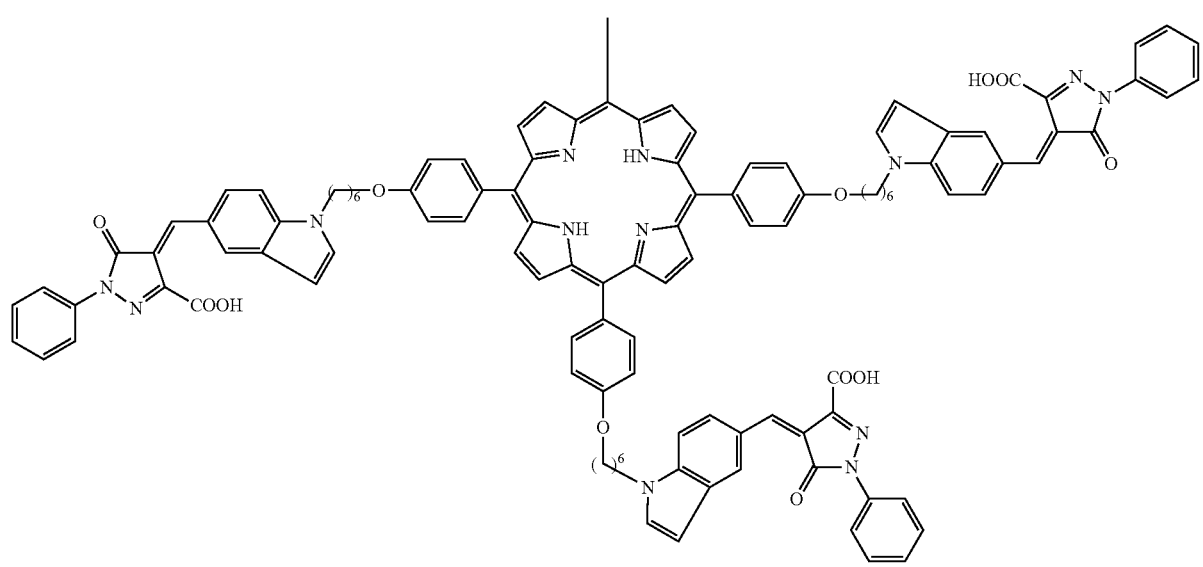

1-10
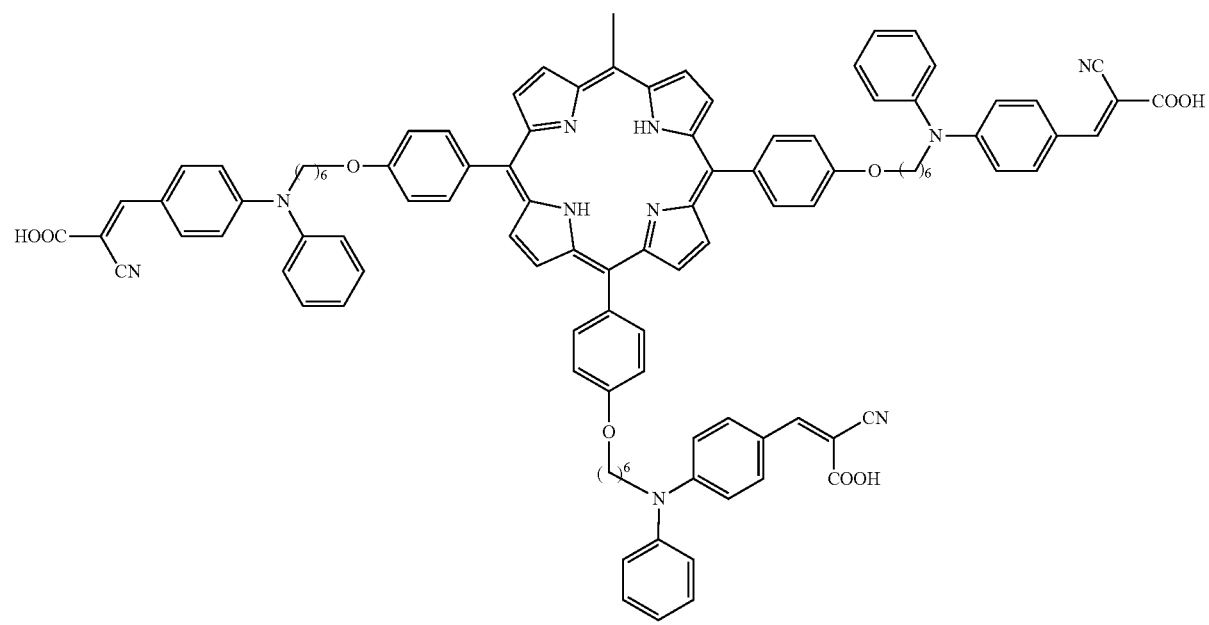
1-11
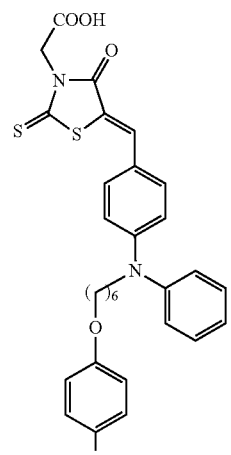

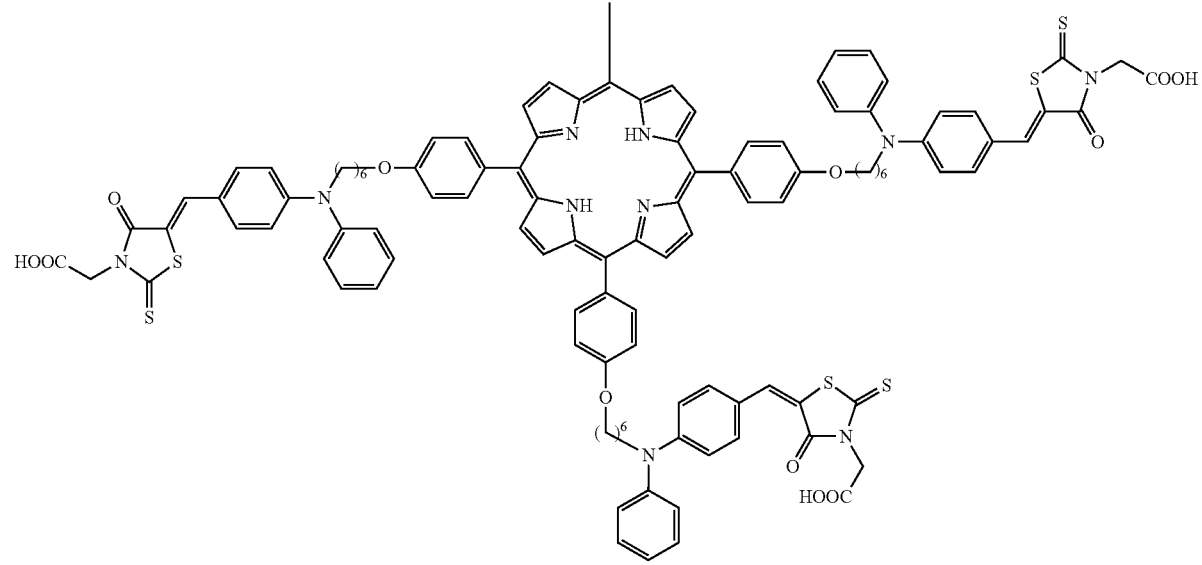
-continued
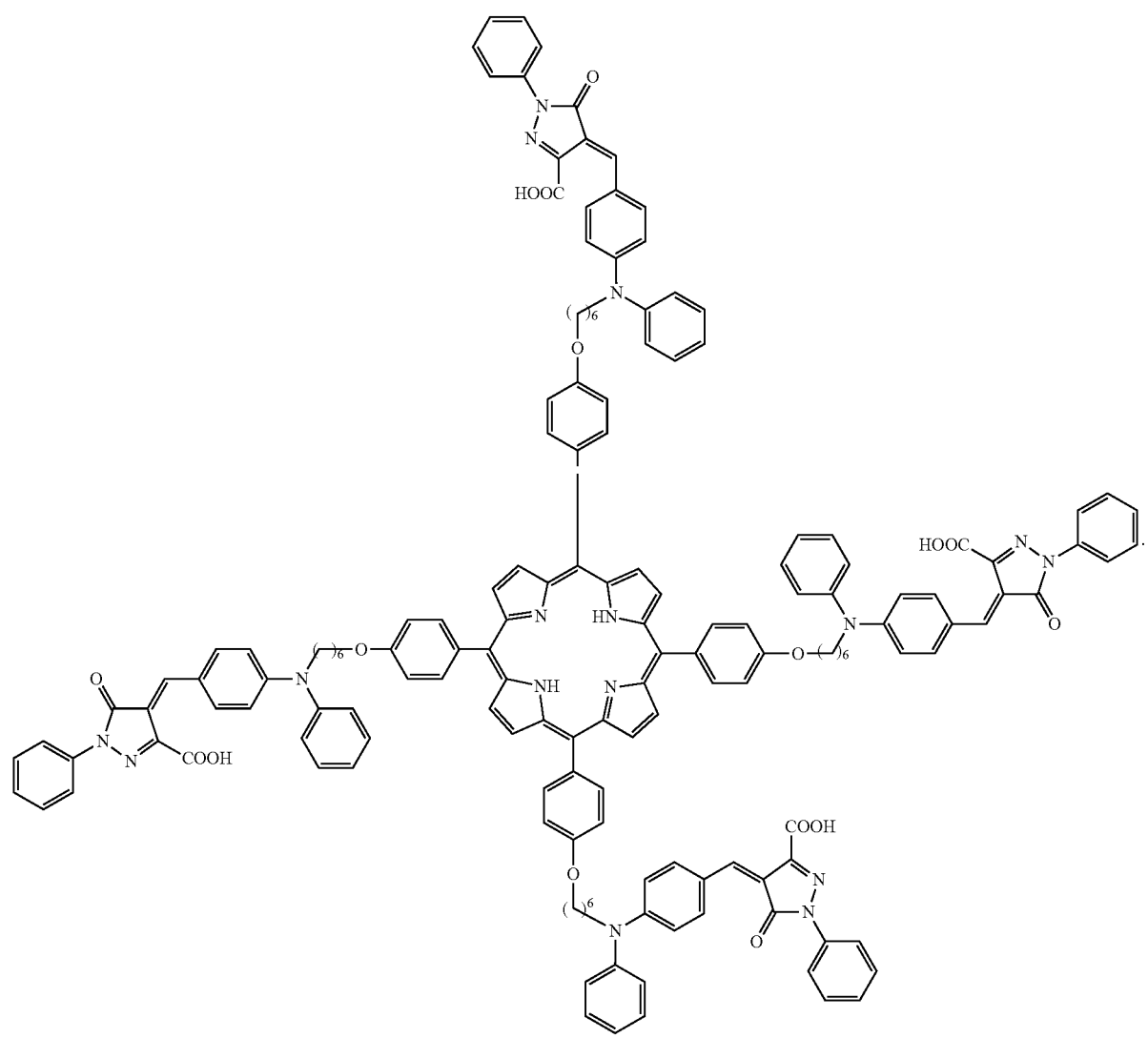
1-12

5. The compound of claim 1, wherein the compound is represented by Chemical Formula 2.
6. The compound of claim 5, wherein the compound represented by Chemical Formula 2 is any one of the following compounds:
2-1
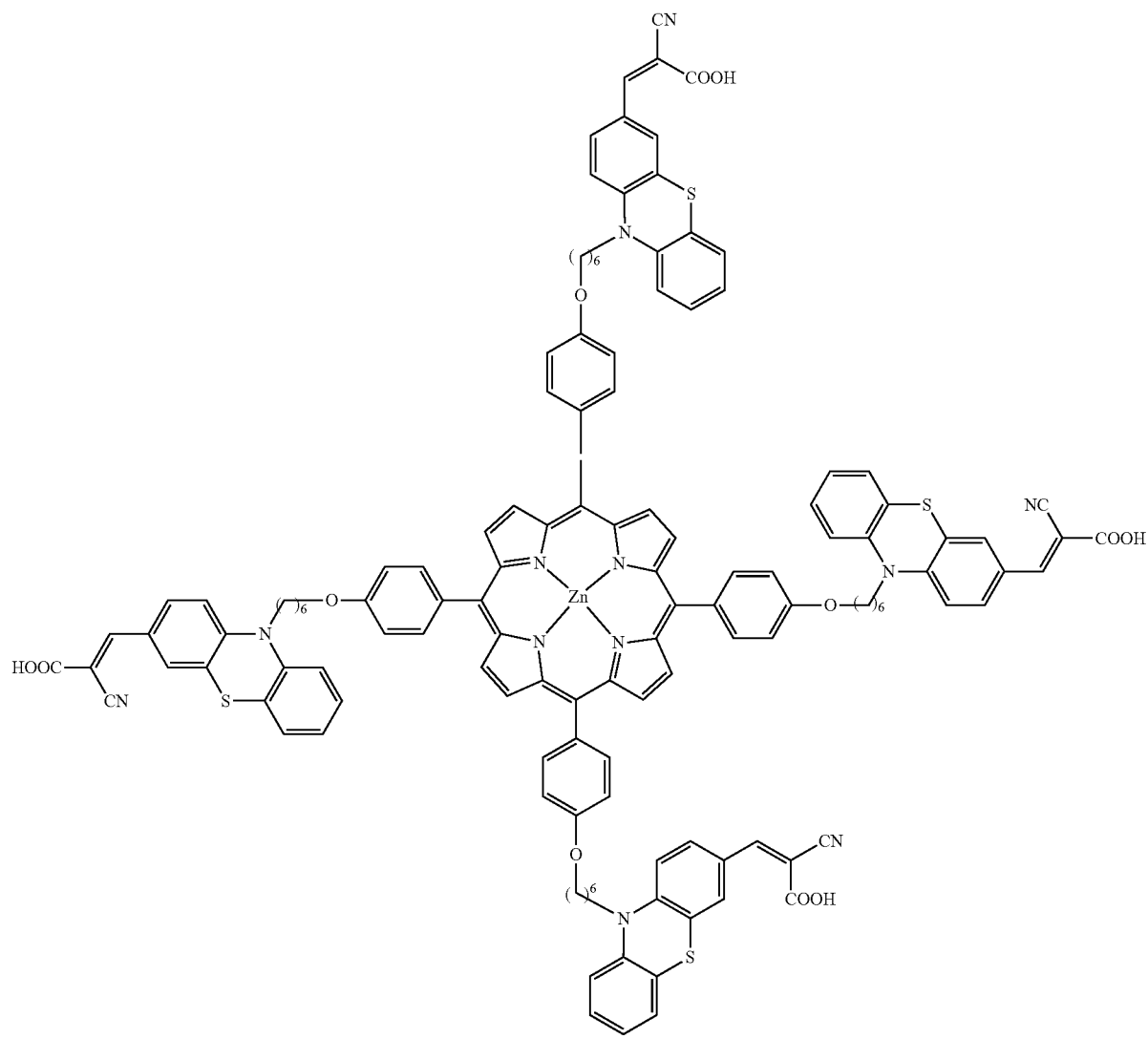
2-2
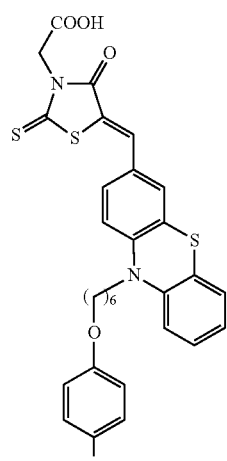

-continued
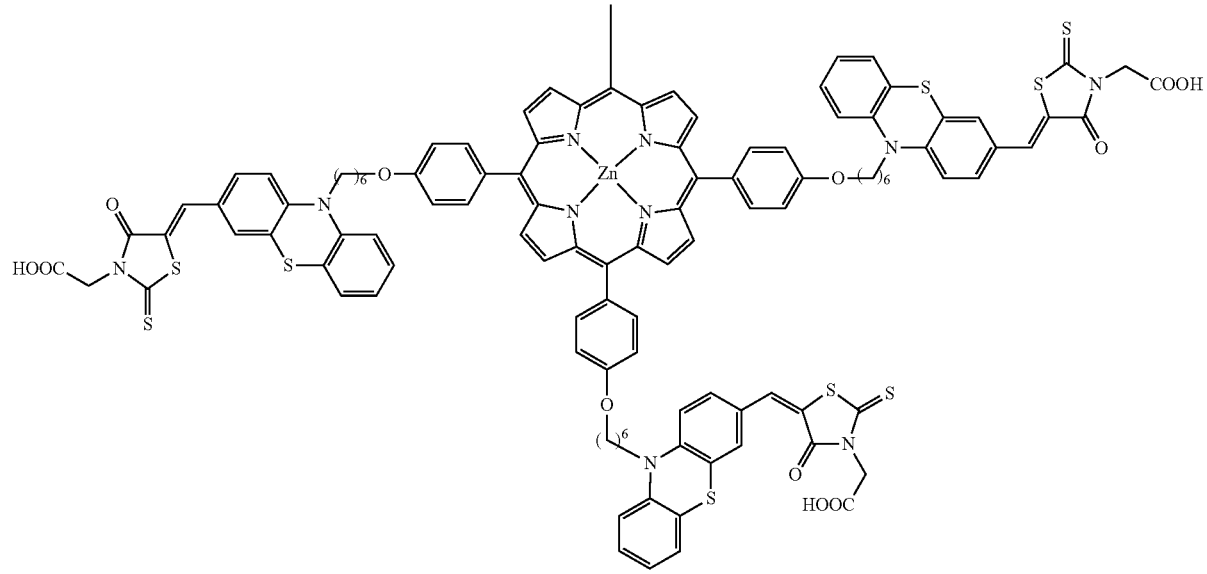
2-3
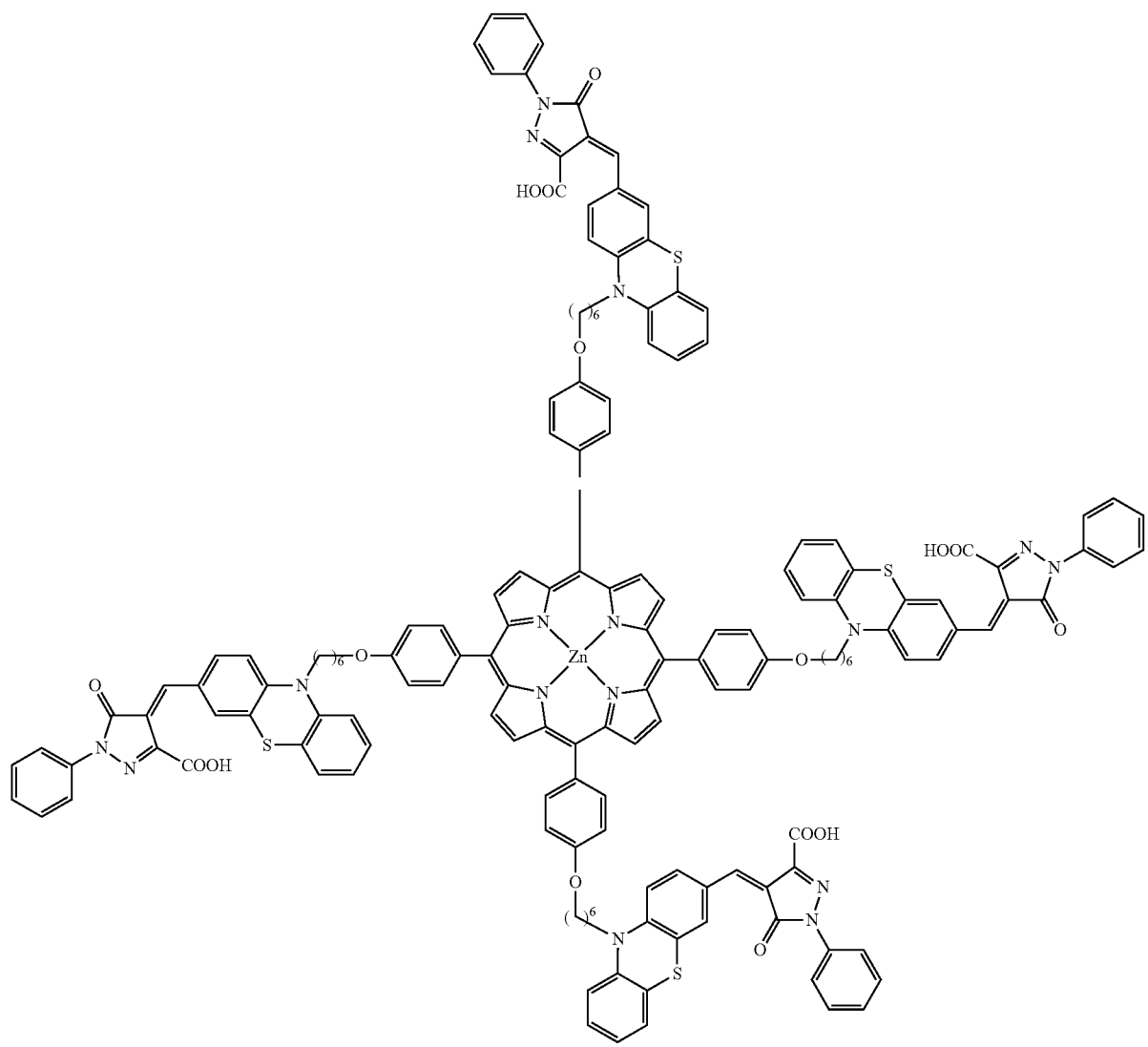

-continued
2-4
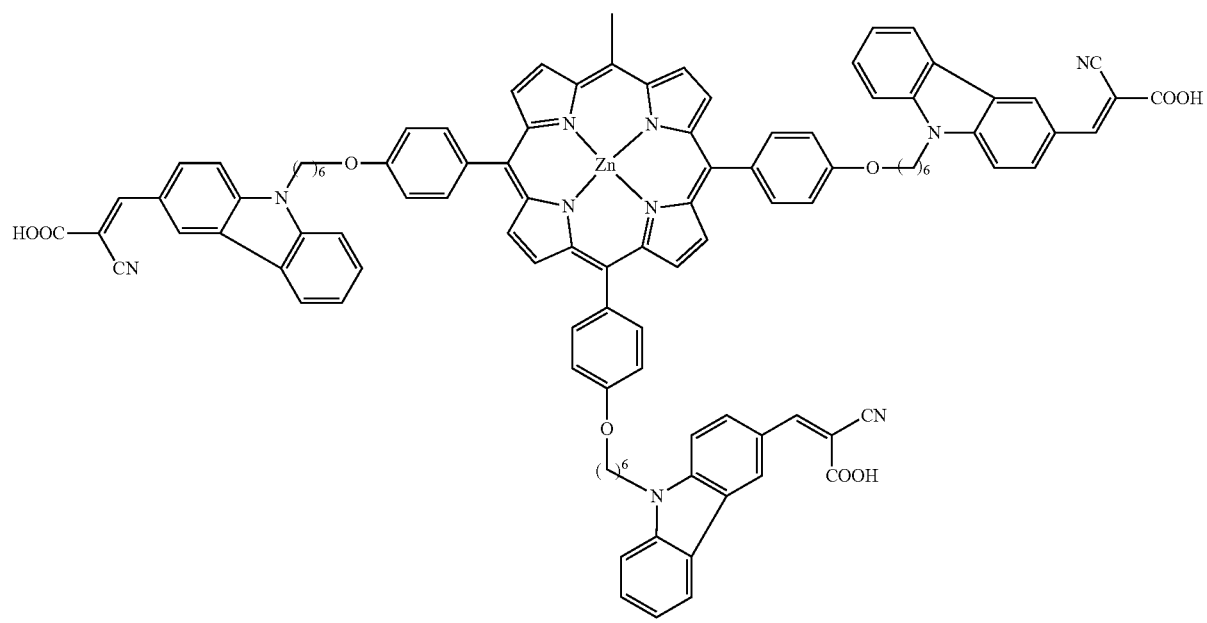
2-5
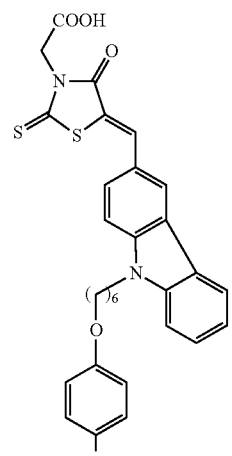

-continued
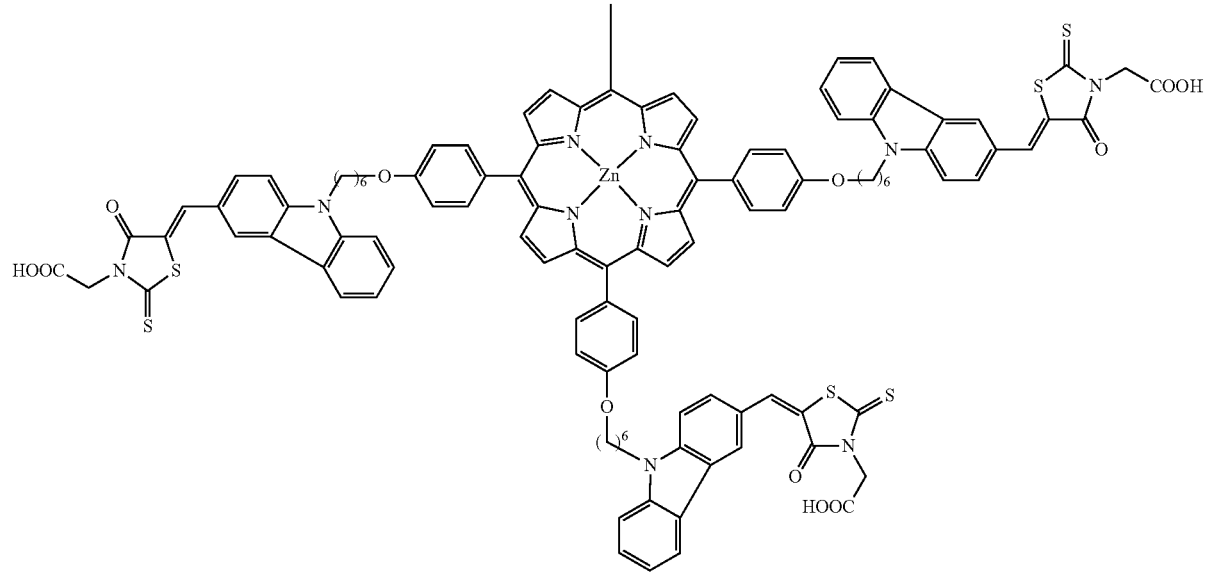
2-6
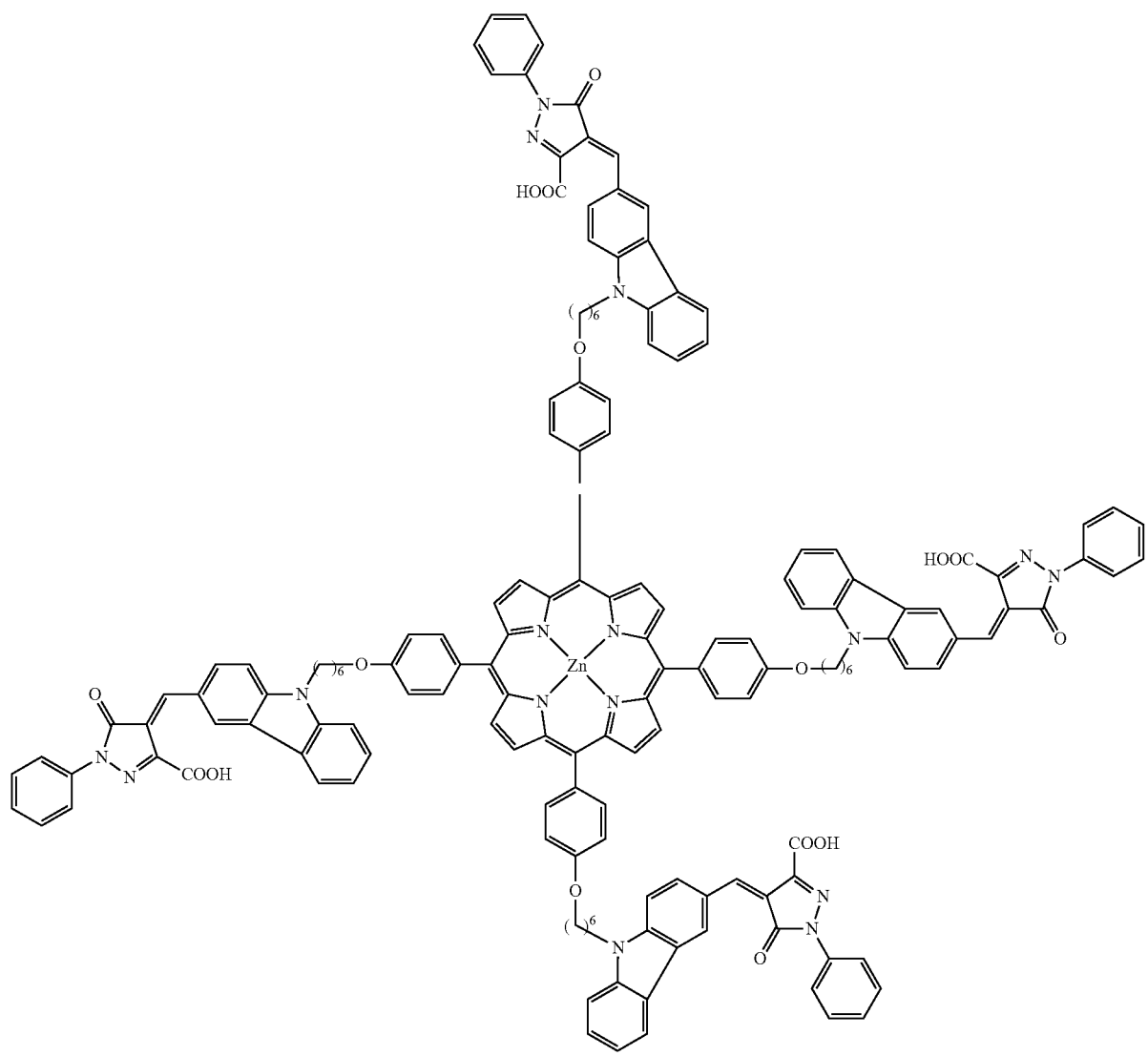

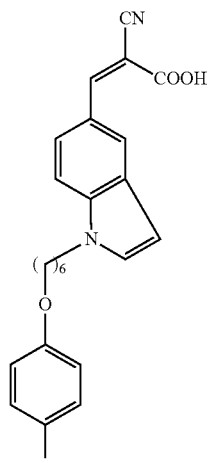
2-7
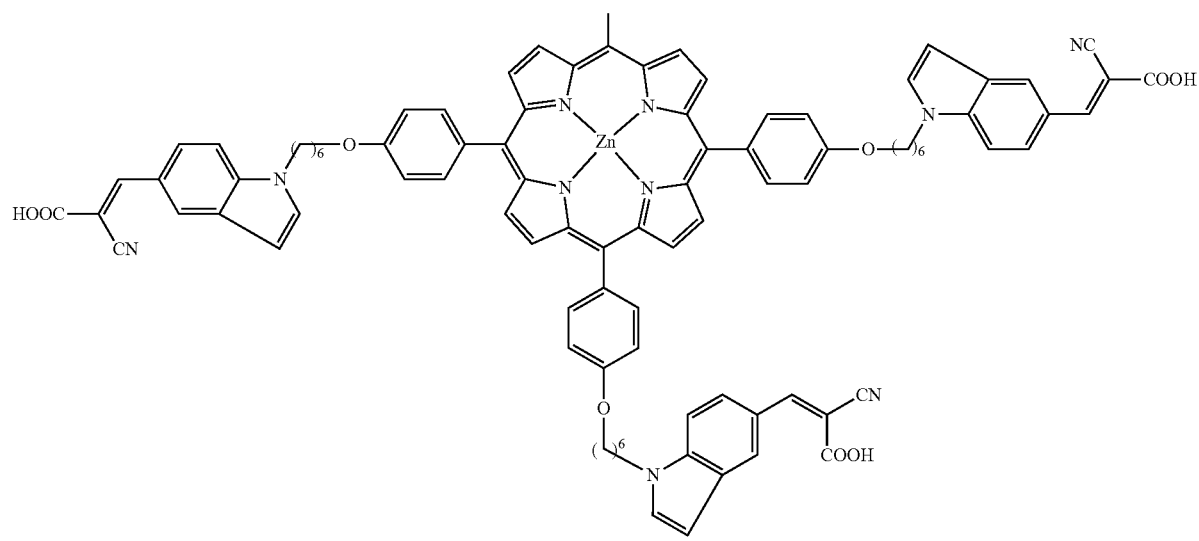
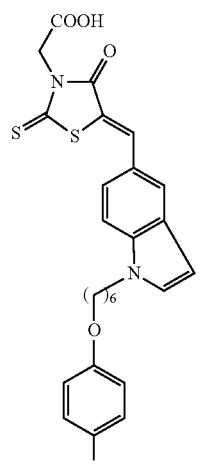
2-8

-continued
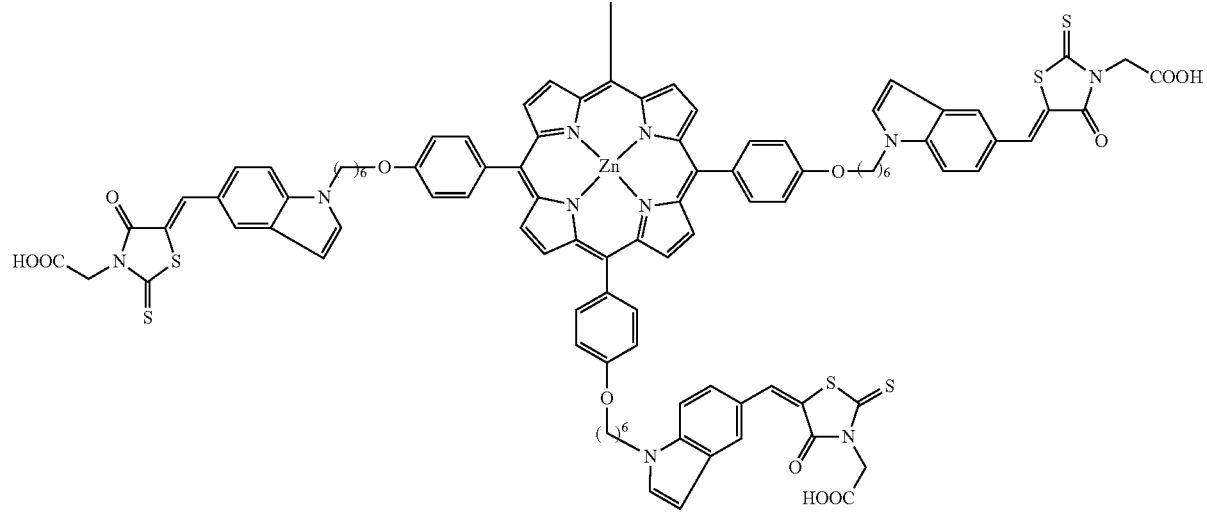
2-9
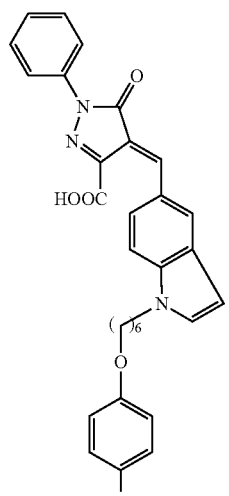
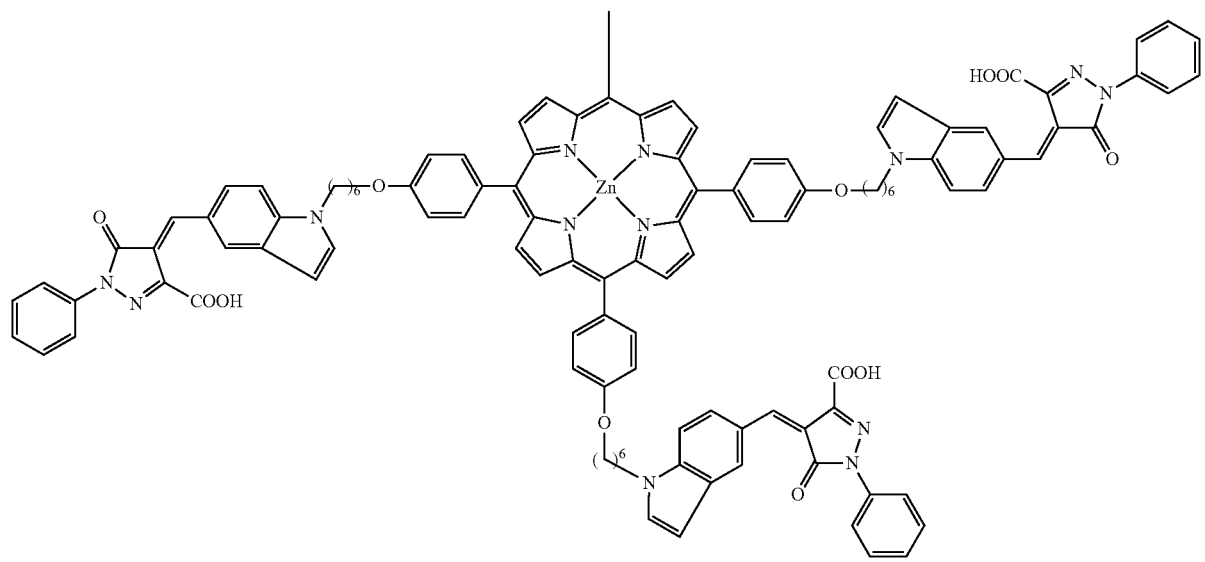

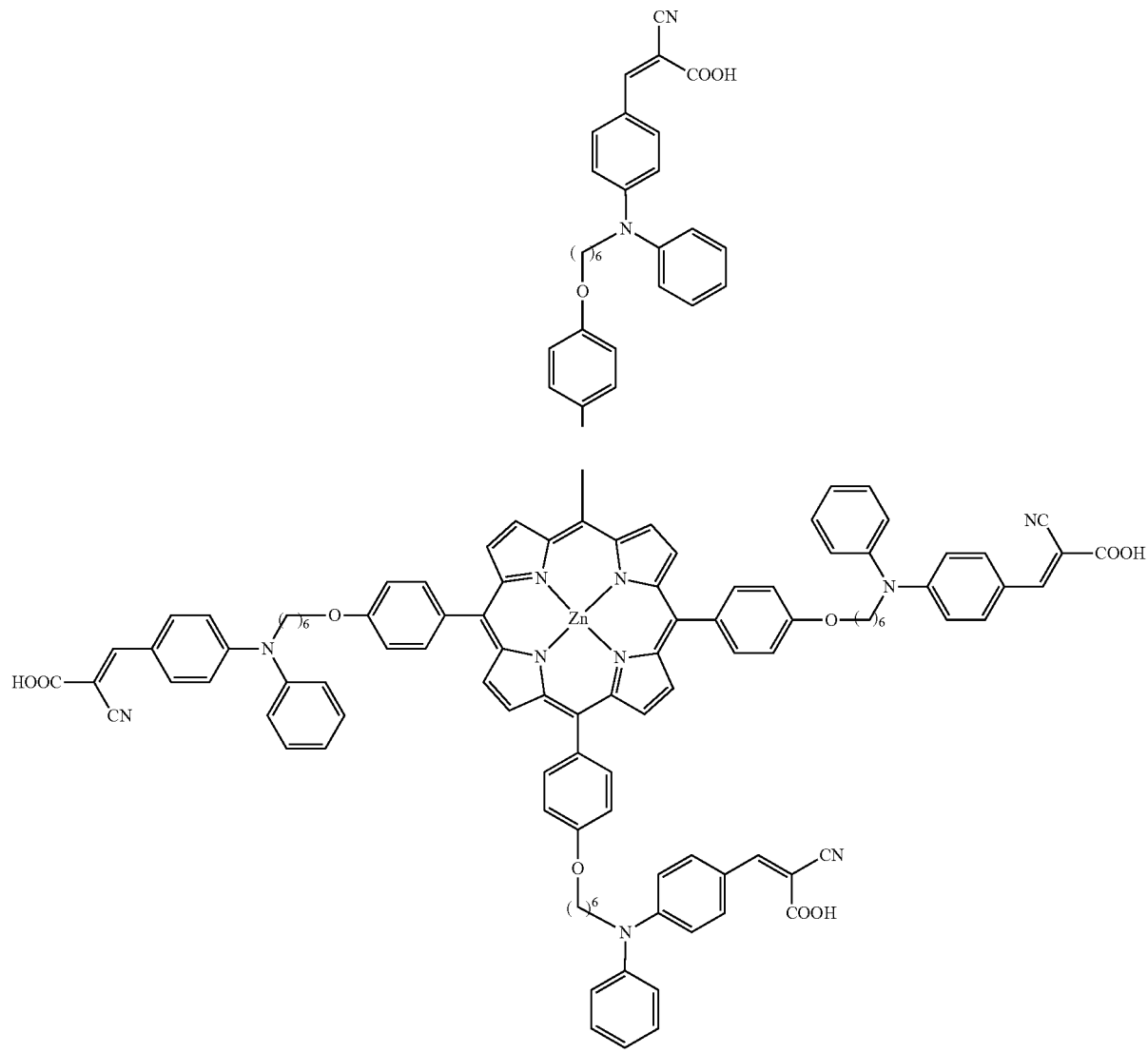
2-10
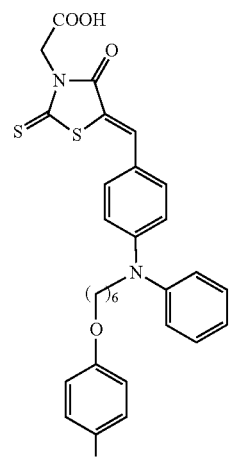
2-11

91
-continued
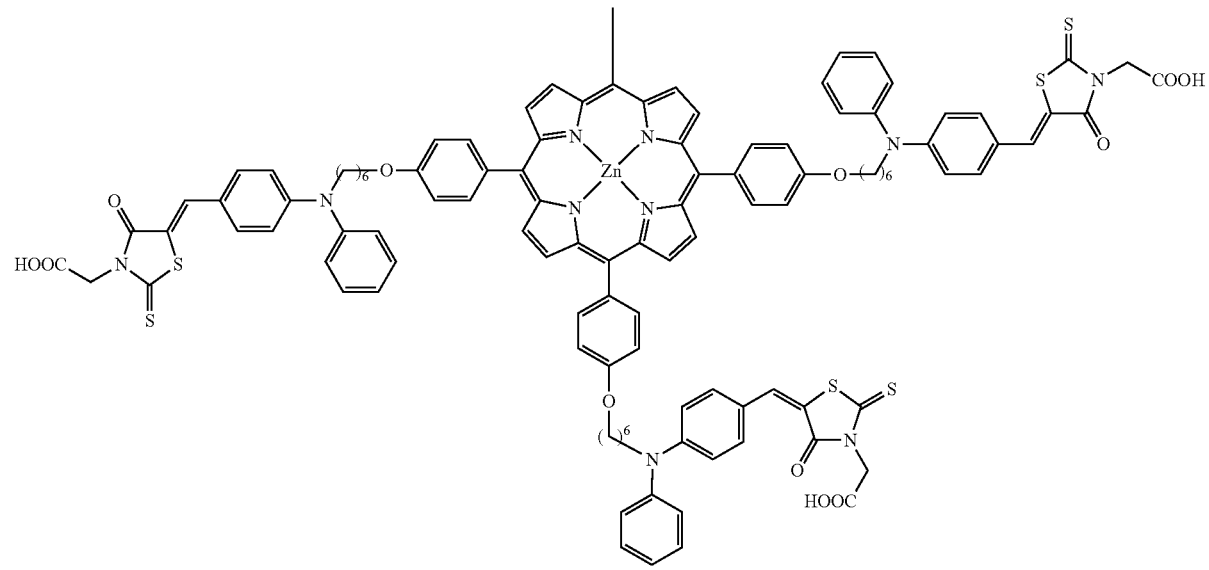
92
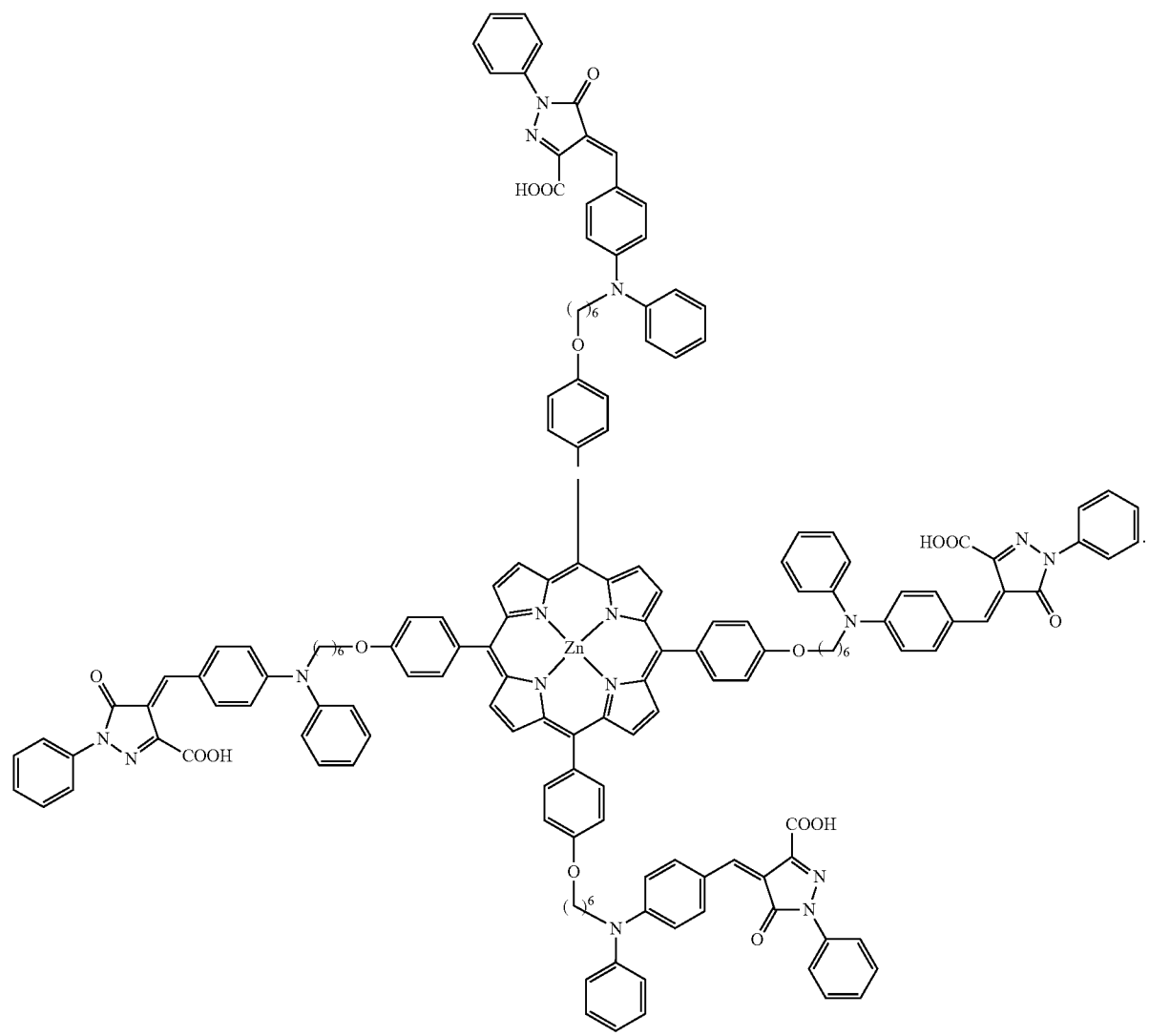
2-12

7. A dye for a dye-sensitized solar cell, comprising the compound of claim 1.

8. A dye-sensitized solar cell, comprising:
a first electrode;
a second electrode; and
a dye layer formed between the first electrode and the second electrode, wherein the dye layer comprises the dye of claim 7.

* * * * *